United States Patent [19]
Sette et al.

[11] Patent Number: 5,736,142
[45] Date of Patent: Apr. 7, 1998

[54] ALTERATION OF IMMUNE RESPONSE USING PAN DR-BINDING PEPTIDES

[75] Inventors: Alessandro Sette, La Jolla; Federico Gaeta, Foster City; Howard M. Grey; John Sidney, both of La Jolla; Jeffrey L. Alexander, Encinita, all of Calif.

[73] Assignee: Cytel Corporation, San Diego, Calif.

[21] Appl. No.: 305,871

[22] Filed: Sep. 14, 1994

Related U.S. Application Data

[63] Continuation-in-part of Ser. No. 121,101, Sep. 14, 1993, abandoned.

[51] Int. Cl.$^6$ .............................. A61K 38/00; C07K 7/02; C07K 7/04
[52] U.S. Cl. .................................. 424/185.1; 424/184.1; 424/193.1; 530/300; 530/327; 530/332; 530/868; 514/2; 514/15
[58] Field of Search ..................... 424/185.1, 186.1, 424/193.1; 530/300, 326–328, 402, 403, 868, 327, 332; 514/2, 15

[56] References Cited

PUBLICATIONS

Brown, Jerry H., et al. (1993) "Three–dimensional structure of the human class II histocompatibility antigen HLS–DR1", *Nature* 364:33–39.

Krieger, Jeffrey L., et al. (1991) "Single Amino Acid Changes in DR and Antigen Define Residues Critical For Peptide–MHC and T Cell Recognition", *Journal of Immunology*, 146:2331–2340.

O'Sullivan, Deirdre, et al. (1991) "Truncation Analysis of Several DR Binding Epitopes", *The Journal of Immunology*, 146:1240–1246.

O'Sullivan, Deirdre, et al. (1991) "On the Interaction of Promiscuous Antigenic Peptides With Different DR Alleles", *The Journal of Immunology*, 147: 2663–2669.

Busch, Robert, et al. (1990) "Degenerate binding of Immunogenic peptides to HLA–DR proteins on B cell surfaces", *International Immunology*, 2:443–451.

Panina–Bordignon, Paola, et al. (1989) "Universally immunogenic T cell epitopes: promiscuous binding to human MHC class II and promiscuous recognition by T cells", *Eur. J. Immunol.*, 19:2237–2242.

Sinigaglia, F., et al. (1988) "A malaria T–cell epitope recognized in association with most mouse and human MHC class II molecules", *Nature*, 336:778–780.

Roche, Paul, et al. (1990) "High–Affinity Binding of an Influenza Hemagglutinin–Derived Peptide to Purified HLS–DR", *The Journal of Immunology*, 144:1849–1856.

Hill, Mark C., et al. (1991) "Conformational and Structural Characteristics of Peptides Binding to HLA–DR Molecules", *The Journal of Immunol.* 147:189–197.

*Primary Examiner*—Thomas M. Cunningham
*Attorney, Agent, or Firm*—Townsend and Townsend and Crew LLP

[57] ABSTRACT

The present invention provides compositions and methods of inhibiting or inducing activation of T cells in a patient. The methods comprise administering a therapeutically effective dose of pharmaceutical compositions comprising a pharmaceutically acceptable carrier and peptides of between about 4 and about 20 residues, that bind antigen binding sites on MHC molecules encoded by substantially all alleles of a DR locus. These peptides are referred to as pan DR binding peptides. The pan DR binding peptides can be used to inhibit immune responses associated with immunopathologies, such as autoimmunity, allograft rejection and allergic responses. The peptides can also be used in combination with CTL peptides to enhance a CTL response.

56 Claims, 4 Drawing Sheets

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
( A ) LENGTH: 13 amino acids
( B ) TYPE: amino acid
( C ) STRANDEDNESS:

(D) TOPOLOGY: linear (ii) MOLECULE TYPE: peptide (xi) SEQUENCE DESCRIPTION: SEQ ID NO:1:

```
Pro Lys Tyr Val Lys Gln Asn Thr Leu Lys Leu Ala Thr
1               5                   10
```

(2) INFORMATION FOR SEQ ID NO:2:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:2:

```
Gly Arg Thr Gln Asp Glu Asn Pro Val Trp His Phe Phe Lys Asn Ile
1               5                   10                  15
Val Thr Pro Arg Thr Pro Pro Pro
                20
```

(2) INFORMATION FOR SEQ ID NO:3:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:3:

```
Tyr Lys Thr Ile Ala Phe Asp Glu Glu Ala Arg Arg
1               5                   10
```

(2) INFORMATION FOR SEQ ID NO:4:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

```
Tyr Ala Arg Phe Gln Ser Gln Thr Thr Leu Lys Gln Lys Thr
1               5                   10
```

(2) INFORMATION FOR SEQ ID NO:5:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:5:

```
Gln Tyr Ile Lys Ala Asn Ser Lys Phe Ile Gly Ile Thr Glu
1               5                   10
```

(2) INFORMATION FOR SEQ ID NO:6:

(i) SEQUENCE CHARACTERISTICS:

(A) LENGTH: 13 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:6:

Asn Gly Gln Ile Gly Asn Asp Pro Asn Arg Asp Ile Leu
1               5                   10

(2) INFORMATION FOR SEQ ID NO:7:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:7:

Tyr Ala His Ala Ala His Ala Ala His Ala Ala His Ala Ala His Ala
1               5                   10                  15

Ala (2) INFORMATION FOR SEQ ID NO:8:

(i) SEQUENCE CHARACTERISTICS:
(A) LENGTH: 14 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:8:

Ile Ser Gln Ala Val His Ala Ala His Ala Glu Ile Asn Glu
1               5                   10

(2) INFORMATION FOR SEQ ID NO:9:

(i) SEQUENCE CHARACTERISTICS:
(A) LENGTH: 16 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:9:

Tyr Leu Glu Asp Ala Arg Arg Leu Lys Ala Ile Tyr Glu Lys Lys Lys
1               5                   10                  15

(2) INFORMATION FOR SEQ ID NO:10:

(i) SEQUENCE CHARACTERISTICS:
(A) LENGTH: 17 amino acids
(B) TYPE: amino acid
(C) STRANDEDNESS:
(D) TOPOLOGY: linear (ii) MOLECULE TYPE: peptide (xi) SEQUENCE DESCRIPTION: SEQ ID NO:10:

Tyr Asn Thr Asp Gly Ser Thr Asp Tyr Gly Ile Leu Gln Ile Asn Ser
1               5                   10                  15

Arg ( 2 ) INFORMATION FOR SEQ ID NO:11:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:11:

```
Pro  His  His  Thr  Ala  Leu  Arg  Gln  Ala  Ile  Leu  Cys  Trp  Gly  Glu  Leu
1                   5                        10                       15
Met  Thr  Leu  Ala
                20
```

( 2 ) INFORMATION FOR SEQ ID NO:12:

( i ) SEQUENCE CHARACTERISTICS:
        ( A ) LENGTH: 21 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:12:

```
Asp  Ile  Phe  Lys  Lys  Ile  Ala  Lys  Met  Phe  Lys  Ala  Arg  Arg  Val  Phe
1                   5                        10                       15
Asn  Val  Val  Asn  Arg
                20
```

( 2 ) INFORMATION FOR SEQ ID NO:13:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:13:

```
Tyr  Ser  Gly  Pro  Leu  Lys  Ala  Glu  Ile  Ala  Gln  Arg  Leu  Glu  Asp  Val
1                   5                        10                       15
```

( 2 ) INFORMATION FOR SEQ ID NO:14:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:14:

```
Thr  Pro  Pro  Ala  Tyr  Arg  Pro  Pro  Asn  Ala  Pro  Ile  Leu
1                   5                        10
```

( 2 ) INFORMATION FOR SEQ ID NO:15:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:15:

```
His Ser Leu Gly Lys Trp Leu Gly His Pro Asp Lys Phe
1               5                   10
```

( 2 ) INFORMATION FOR SEQ ID NO:16:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:16:

```
Asn Thr Asp Gly Ser Thr Asp Tyr Gly Ile Leu Gln Ile Asn Ser Arg
1               5                   10                  15
```

( 2 ) INFORMATION FOR SEQ ID NO:17:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:17:

```
Trp Thr Leu Lys
1
```

( 2 ) INFORMATION FOR SEQ ID NO:18:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1..13
        ( D ) OTHER INFORMATION: /note="Peptide wherein X is
            tyrosine or phenylalanine."

( x i ) SEQUENCE DESCRIPTION: SEQ ID NO:18:

```
Ala Ala Xaa Ala Ala Ala Lys Thr Ala Ala Ala Ala
1               5                   10
```

( 2 ) INFORMATION FOR SEQ ID NO:19:

( i ) SEQUENCE CHARACTERISTICS:
        ( A ) LENGTH: 13 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1..13
        ( D ) OTHER INFORMATION: /note="Peptide wherein X is
            tyrosine or phenylalanine."

( x i ) SEQUENCE DESCRIPTION: SEQ ID NO:19:

```
Ala Ala Xaa Ala Ala Ala Ala Thr Leu Lys Ala Ala Ala
```

(2) INFORMATION FOR SEQ ID NO:20:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1..13
        (D) OTHER INFORMATION: /note="Peptide wherein X is tyrosine or phenylalanine."

(xi) SEQUENCE DESCRIPTION: SEQ ID NO:20:

Ala Ala Xaa Val Ala Ala Ala Thr Leu Lys Ala Ala Ala
1               5                   10

(2) INFORMATION FOR SEQ ID NO:21:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1..13
        (D) OTHER INFORMATION: /note="Peptide wherein X is tyrosine or phenylalanine."

(xi) SEQUENCE DESCRIPTION: SEQ ID NO:21:

Ala Ala Xaa Ile Ala Ala Ala Thr Leu Lys Ala Ala Ala
1               5                   10

(2) INFORMATION FOR SEQ ID NO:22:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1..13
        (D) OTHER INFORMATION: /note="Peptide wherein X is tyrosine or phenylalanine."

(xi) SEQUENCE DESCRIPTION: SEQ ID NO:22:

Ala Lys Xaa Val Ala Ala Trp Thr Leu Lys Ala Ala Ala
1               5                   10

(2) INFORMATION FOR SEQ ID NO:23:

(i) SEQUENCE CHARACTERISTICS:
        (A) LENGTH: 13 amino acids
        (B) TYPE: amino acid
        (C) STRANDEDNESS:
        (D) TOPOLOGY: linear (ii) MOLECULE TYPE: peptide (ix) FEATURE:

(A) NAME/KEY: Modified-site
(B) LOCATION: 1..13
(D) OTHER INFORMATION: /note="Peptide wherein X is tyrosine or phenylalanine."

(xi) SEQUENCE DESCRIPTION: SEQ ID NO:23:

Ala Lys Phe Val Ala Ala Trp Thr Leu Lys Ala Ala Ala
1               5                   10

(2) INFORMATION FOR SEQ ID NO:24:

(i) SEQUENCE CHARACTERISTICS:
    (A) LENGTH: 13 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 1..13
    (D) OTHER INFORMATION: /note="Peptide wherein X is tyrosine or phenylalanine."

(xi) SEQUENCE DESCRIPTION: SEQ ID NO:24:

Ala Ala Xaa Ala Glu Ala Ala Thr Leu Lys Ala Ala Ala
1               5                   10

(2) INFORMATION FOR SEQ ID NO:25:

(i) SEQUENCE CHARACTERISTICS:
    (A) LENGTH: 13 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 1..13
    (D) OTHER INFORMATION: /note="Peptide wherein X is tyrosine or phenylalanine."

(xi) SEQUENCE DESCRIPTION: SEQ ID NO:25:

Ala Ala Xaa Ala Val Ala Ala Thr Leu Lys Ala Ala Ala
1               5                   10

(2) INFORMATION FOR SEQ ID NO:26:

(i) SEQUENCE CHARACTERISTICS:
    (A) LENGTH: 13 amino acids
    (B) TYPE: amino acid
    (C) STRANDEDNESS:
    (D) TOPOLOGY: linear (ii) MOLECULE TYPE: peptide (ix) FEATURE:
    (A) NAME/KEY: Modified-site
    (B) LOCATION: 1..13
    (D) OTHER INFORMATION: /note="Peptide wherein X is tyrosine or phenylalanine."

(xi) SEQUENCE DESCRIPTION: SEQ ID NO:26:

Ala Ala Xaa Ala Ala Glu Ala Thr Leu Lys Ala Ala Ala
1               5                   10

(2) INFORMATION FOR SEQ ID NO:27:

(i) SEQUENCE CHARACTERISTICS:

(A) LENGTH: 13 amino acids
        (B) TYPE: amino acid
        (C) STRANDEDNESS:
        (D) TOPOLOGY: linear (i i) MOLECULE TYPE: peptide (i x) FEATURE:
        (A) NAME/KEY: Modified-site
        (B) LOCATION: 1..13
        (D) OTHER INFORMATION: /note="Peptide wherein X is
            tyrosine or phenylalanine."

(x i) SEQUENCE DESCRIPTION: SEQ ID NO:27:

Ala  Ala  Xaa  Ala  Ala  Val  Ala  Thr  Leu  Lys  Ala  Ala  Ala
    1              5                        10

(2) INFORMATION FOR SEQ ID NO:28:

(i) SEQUENCE CHARACTERISTICS:
        (A) LENGTH: 13 amino acids
        (B) TYPE: amino acid
        (C) STRANDEDNESS:
        (D) TOPOLOGY: linear (i i) MOLECULE TYPE: peptide (i x) FEATURE:
        (A) NAME/KEY: Modified-site
        (B) LOCATION: 1..13
        (D) OTHER INFORMATION: /note="Peptide wherein X is
            tyrosine or phenylalanine."

(x i) SEQUENCE DESCRIPTION: SEQ ID NO:28:

Ala  Ala  Xaa  Ala  Ala  Ala  Glu  Thr  Leu  Lys  Ala  Ala  Ala
    1              5                        10

(2) INFORMATION FOR SEQ ID NO:29:

(i) SEQUENCE CHARACTERISTICS:
        (A) LENGTH: 13 amino acids
        (B) TYPE: amino acid
        (C) STRANDEDNESS:
        (D) TOPOLOGY: linear (i i) MOLECULE TYPE: peptide (i x) FEATURE:
        (A) NAME/KEY: Modified-site
        (B) LOCATION: 1..13
        (D) OTHER INFORMATION: /note="Peptide wherein X is
            tyrosine or phenylalanine."

(x i) SEQUENCE DESCRIPTION: SEQ ID NO:29:

Ala  Ala  Xaa  Ala  Ala  Ala  Val  Thr  Leu  Lys  Ala  Ala  Ala
    1              5                        10

ALTERATION OF IMMUNE RESPONSE USING PAN DR-BINDING PEPTIDES

This application is a continuation-in-part of application U.S. Ser. No. 08/121,101 filed Sep. 14, 1993, now abandoned, which is incorporated herein by reference.

BACKGROUND OF THE INVENTION

The present invention relates to compositions and methods for preventing, treating or diagnosing a number of pathological states such as autoimmune diseases, viral diseases and cancers. In particular, it provides novel peptides capable of binding selected major histocompatibility complex (MHC) molecules and either inducing or inhibiting an immune response.

MHC molecules are classified as either Class I or Class II molecules. Class II MHC molecules are expressed by specialized antigen presenting cells (APC) such as macrophages, dendritic cells, or B cells. The Class II MHC molecules usually associate with peptide fragments derived from processing of protein antigens which enter the endocytic pathway from the APC exterior. The MHC-peptide complexes are subsequently presented for scrutiny to CD4+ T helper cells which are then activated, proliferate and amplify the immune response to the particular immunogenic peptide that is displayed. Activation of T cells requires engagement of the T Cell Receptor (TCR) by its ligand, a bi-molecular complex of an MHC molecule and a peptide antigen (Shimonkevitz, et al., *J. Immunol.* 133, 2067–2074 (1984); Babbitt, et al., *Nature* 317, 359–361 (1985); Buus, et al., *Cell* 47, 1071–1077 (1986); Townsend, A., and Bodmer, H., *Annu. Rev. Immunol.* 7, 601–624.

Inappropriate activation of T cells is a component of a number of immunopathologies, such as autoimmunity, allograft rejection and allergic responses. Exemplary autoimmune diseases include rheumatoid arthritis, multiple sclerosis, and myasthenia gravis. Allergic responses involving T cell activation include allergies to various pollens, dust mites and the like. In addition, foreign infectious diseases may cause immunopathology (e.g., lyme disease, hepatitis, LCMV, post-streptococcal endocarditis, or glomerulonephritis). Food hypersensitivities, such as celiac disease and Crohn's disease, as well as other allergic diseases, have been associated with particular MHC alleles or suspected of having an autoimmune component.

The most commonly used approach to treating these conditions is to suppress the immune system, typically by using immunosuppressive drugs. Another approach has been proposed for cases in which the MHC allele associated with the condition is known, involving selective blockade of a given MHC allele. However, where a number of MHC restrictions are involved, approaches other than selective blockade must be found.

Immunochemical studies of the requirements for peptide binding to class II molecules have been carried out. The binding motifs of several murine and human class II MHC alleles have been defined, and motif analysis by sequencing of naturally processed peptides has also recently been described for various class II types (Rudensky et al., *Nature* 353, 622–627 (1991); Chicz et al., *Nature* 358, 764–768 (1992); Hunt et al., *Science* 256, 1817–1820 (1992); Rudensky et al., *Nature* 359, 429–431 (1992)).

In the case of DR molecules in particular, it has been shown (Brown et al., *Nature* 364, 33–39 (1993)) that a large hydrophobic anchor engaging a corresponding hydrophobic pocket of the MHC binding groove is the most crucial determinant of peptide-DR interactions. Several other anchors play definite, albeit less prominent roles and help determine allelic specificity. Recently it has also been emphasized that the peptide backbone of the C-terminal half of the peptide molecule is engaged in direct hydrogen bonding with the walls of the MHC binding groove (Krieger et al., *J. Immunol.* 146, 2331–2340 (1991)); O'Sullivan et al., *J. Immunol.* 146, 1240–1246 (1991); and O'Sullivan et al., *J. Immunol.* 147, 2663–2669 (1991).

Although allele-specific polymorphic residues that line the peptide binding pockets of MHC alleles tend to endow each allele with the capacity to bind a unique set of peptides, there are many instances in which a given peptide has been shown to bind to more than one MHC specificity. This has been best documented in the case of the human DR isotype, in which it has been noted that several DR alleles appear to recognize similar motifs, and independently, several investigators reported degenerate binding and/or recognition of certain epitopes in the context of multiple DR types, leading to the concept that certain peptides might represent "universal" epitopes (Busch et al., *Int. Immunol.* 2,443–451 (1990); Panina-Bordignon et al., *Eur. J. Immunol.* 19, 2237–2242 (1989); Sinigaglia et al., *Nature* 336, 778–780 (1988); O'Sullivan et al., *J. Immunol.* 147, 2663–2669 (1991) Roache et al., *J. Immunol.* 144, 1849–1856 (1991); Hill et al., *J. Immunol.* 147, 189–197 (1991)). However, although the previously reported epitopes do have the capacity to bind to several DR alleles, they are by no means universal.

Accordingly, the present invention provides DR binding peptides, called "pan DR binding peptides" that are recognized by a broad pattern of DR alleles. According to the present invention such Pan DR binding peptides may be used as potent immunogens for class II restricted T cells, and as a useful human peptide-based immunosuppressant, vaccine or therapeutic agent.

SUMMARY OF THE INVENTION

The present invention provides compositions and methods of inhibiting or inducing activation of T cells in a patient. The methods comprise administering a therapeutically effective dose of pharmaceutical compositions comprising a pharmaceutically acceptable carrier and peptides of between about 4 and about 20 residues, that bind antigen binding sites on MHC molecules encoded by substantially all alleles of a DR locus. These peptides are referred to as pan DR binding peptides. The pan DR binding peptides can be used to inhibit immune responses associated with immunopathologies, such as autoimmunity, allograft rejection and allergic responses.

When used to enhance an immune response, the pan DR peptide can act as a T helper peptide and be administered with a CTL inducing peptide. The T helper peptide may be linked to the CTL inducing peptide to form a CTL/T helper peptide conjugate. The conjugates may also be further modified. For instance, the conjugate may be acetylated, palmitylated, or acylated with a fatty acid, or linked to a carrier. The CTL peptide may also be linked to the T helper peptide by a spacer molecule, such as Ala-Ala-Ala. Alternatively, pan DR peptides can be used to augment antibody responses. As with the induction of CTL responses, pan DR peptides can be, administered either linked to, or admixed with, antibody inducing determinants.

Pan DR peptides can be described using various conventions. For example, preferred pan DR peptides have the formula $R_1$—$R_2$—$R_3$—$R_4$—$R_5$, proceeding in the direction from the amino-terminus of the peptide ($R_1$) to the carboxy-terminus ($R_5$), where $R_1$ is a D-amino acid followed by alanine or lysine; $R_2$ is cyclohexylalanine, tyrosine, or phenylalanine; $R_3$ is 3 or 4 amino acids each of which is independently selected from the group consisting of alanine, isoleucine, serine and valine; $R_4$ is threonine-leucine-lysine, lysine-theronine, or tryptophan-threonine-leucine-lysine; and $R_5$ consists of 2 to 4 amino acids followed by a D-amino acid, where each of the 2 or 4 amino acids is independently selected from the group consisting of alanine, serine and valine. According to this formula, more preferred pan DR peptides have the formula $R_1$—$R_2$—$R_3$—$R_4$—$R_5$, where $R_1$ is D-alanine followed by alanine or lysine; $R_2$ is cyclohexylalanine or phenylalanine; R3 is 3 or 4 amino acids each of which is selected from the group comprising alanine, isoleucine, and valine; $R_4$ is threonine-leucine-lysine, lysine-theronine, or tryptophan-threonine-leucine-lysine (SEQ NO: 18) and $R_5$ is 2 to 4 alanines followed by D-alanine.

Pan DR peptides can also be described using the one-letter code for amino acids commonly found in proteins and specifying a designation for D-amino acids or unusual amino acids. Using this convention, preferred pan DR peptides of the invention include the following: oZXZZZZKTZZZZo, oZXZZZZTLKZZo, oZXVZZZTLKZZo, oZXIZZZTLKZZo, oKXVZZWTLKZZo, and oKFVZZWTLKZZo wherein o is a D-amino acid, Z is alanine, serine or valine, K is lysine, T is threonine, L is leucine, W is tryptophan, and X is cyclohexylalanine, tyrosine or phenylalanine. Most preferred pan DR peptides include aAXAAAKTAAAAa, aAXAAAATLKAAa, aAXVAAATLKAAa, aAXIAAATLKAAa, aKXVAAWTLKAAa, and aKFVAAWTLKAAa wherein a is D-alanine, A is alanine, X is cyclohexylalanine, K is lysine, T is threonine, L is leucine, V is valine, I is isolucine, W is tryptophan.

BRIEF DESCRIPTION OF THE DRAWINGS

FIG. 2A shows results of a second stimulation, and FIG. 2B shows results of a third stimulation. The maximum A cpm obtained is plotted on the ordinate.

DEFINITIONS

Figure 1A:
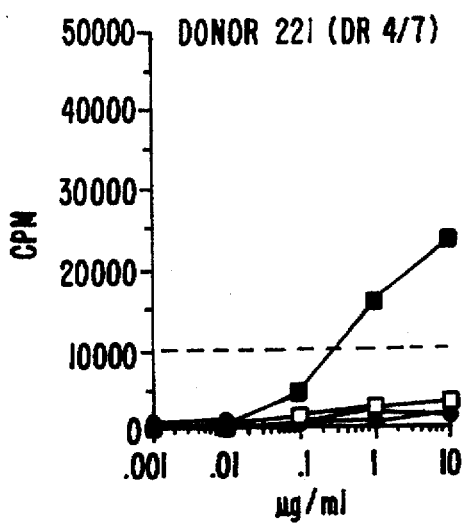
FIGS. 1A–1F show representative responses for three of twelve different donors. Antigen specific T cell responses from human PBMC T cell lines generated on day 0 by addition of either peptide 965.10 (closed square), 906.09 (open square), 760.50 (closed circle), or Tetanus toxoid 830–843 (open circle) as assayed on day 14 (second stimulation, FIGS. 1A, 1B, 1C) and day 28 (third stimulation, FIGS. 1D, 1E, 1F). A representative of two independent experiments is shown.
Figure 1B:
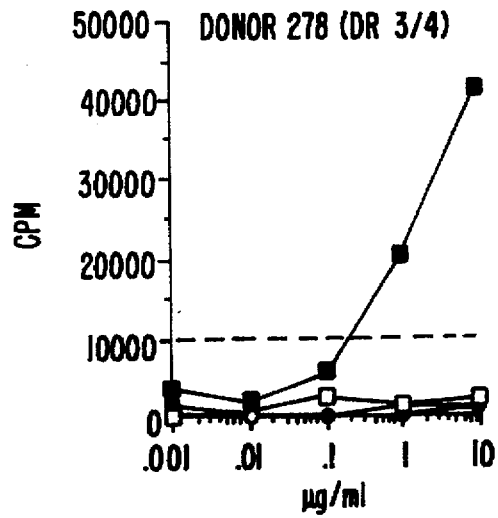
Figure 1C:
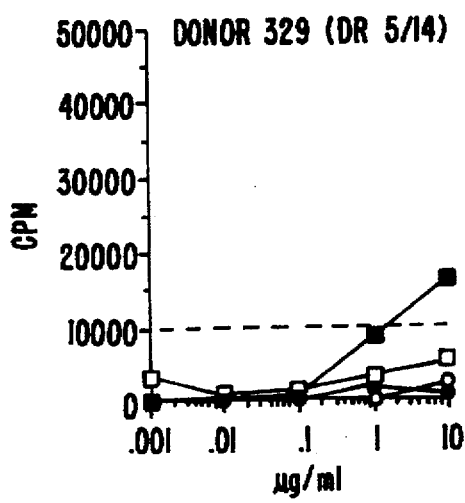
Figure 1D:
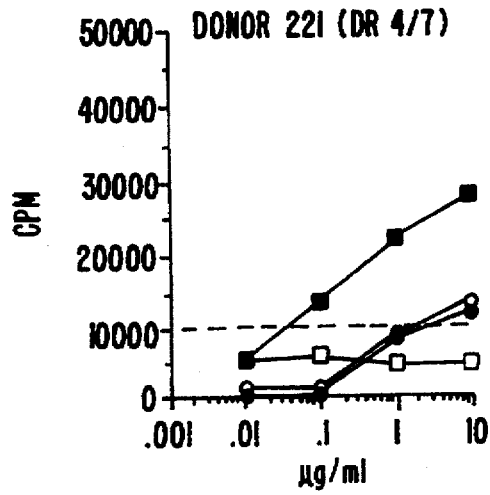
Figure 1E:
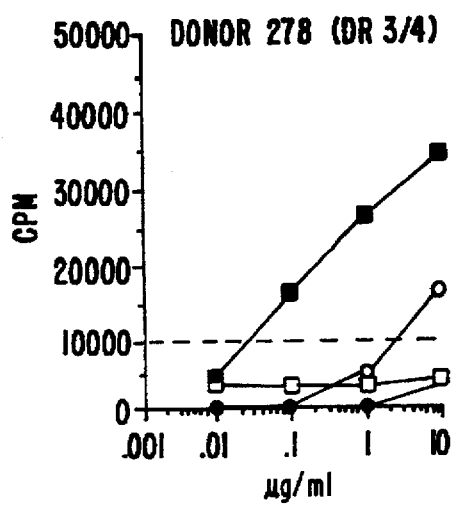
Figure 1F:
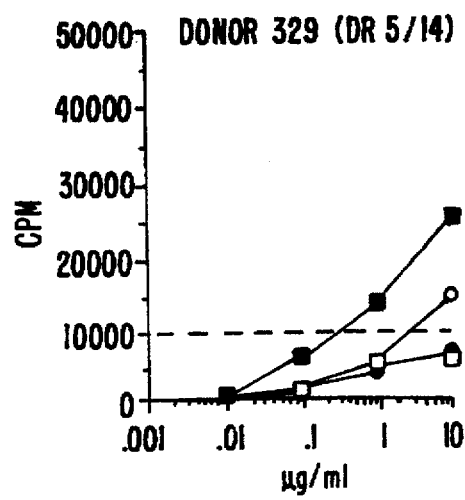

An oligopeptide or peptide as used herein refers to a chain of at least four amino acid or amino acid mimetics, preferably at least six, more preferably eight to ten, sometimes eleven to fourteen residues, and usually fewer than about thirty residues, more usually fewer than about twenty-five, and preferably fewer than fifteen, e.g., eight to fourteen residues. The oligopeptides or peptides can be a variety of lengths, either in their neutral (uncharged) forms or in forms which are salts, and either free of modifications such as glycosylation, side chain oxidation, or phosphorylation or containing these modifications, subject to the condition that the modification not destroy the biological activity of the polypeptides as herein described.

When refering to an amino acid residue in a peptide, oligopeptide or protein the terms "amino acid residue", "amino acid" and "residue" are used interchangably and, as used herein, mean an amino acid or amino acid mimetic joined covalently to at least one other amino acid or amino acid mimetic through an amide bond or amide bond mimetic.

As used herein, the term "amino acid", when unqualified, refers to an "L-amino acid" or L-amino acid mimetic.

Although the peptides will preferably be substantially free of other naturally occurring proteins and fragments thereof, in some embodiments the peptides can be synthetically conjugated to native fragments or particles.

By biological activity is meant the ability to bind an appropriate MHC molecule and, in the case of peptides useful for stimulating CTL responses, induce a T helper response, which in turn helps induce a CTL response against a target antigen or antigen mimetic. In the case of a peptide analog antagonist, the analog will have biological activity if it competes with the native peptide for binding to the MHC molecule and thus substantially reduces the ability of the native peptide to stimulate a T cell response.

A "pan DR-binding peptide" of the invention is a peptide capable of binding at least about 7 of the 12 most common DR alleles (DR1, 2w2b, 2w2a, 3, 4w4, 4w14, 5, 7, 52a, 52b, 52c, and 53) with high affinity. "High affinity" is defined here as binding with an IC50% of less than 300 nM.

Throughout this disclosure, results are expressed in terms of IC50's. Given the conditions in which the assays are run (i.e., limiting MHC and labeled peptide concentrations), these values approximate $K_D$ values. It should be noted that IC50 values can change, often dramatically, if the assay conditions are varied, and depending on the particular reagents used (e.g., MHC preparation, etc.). For example, excessive concentrations of MHC will increase the apparent measured IC50 of a given ligand.

An alternative way of expressing the binding data, to avoid these uncertainties, is as a relative value to a reference peptide. The reference peptide is included in every assay. As a particular assay becomes more, or less, sensitive, the IC50's of the peptides tested may change somewhat. However, the binding relative to the reference peptide will not change. For example, in an assay run under conditions such that the IC50 of the reference peptide increases 10-fold, all IC50 values will also shift approximately 10-fold. Therefore, to avoid ambiguities, the assessment of whether a peptide is a good, intermediate, weak, or negative binder should be based on it's IC50, relative to the IC50 of the standard peptide.

If the IC50 of the standard peptide measured in a particular assay is different from that reported in Table I,

TABLE I

| Allele | Assay standard | Sequence | SEQ. ID NO: | Avg. IC50 nM |
|---|---|---|---|---|
| DR1 | HA 307–319 | PKYVKQNTLKLAT | SEQ. ID NO: 1 | 5 |
| DR2w2b | MBP 78–101 | GRTQDENPVWHFFKNIVTPRTPPP | SEQ. ID NO: 2 | 9.1 |
| DR3 | MT 65 kd 3–13 | YKTIAFDEEARR | SEQ. ID NO: 3 | 250 |
| DR4w4 | HA 307–319 | PKYVKQNTLKLAT | SEQ. ID NO: 1 | 45 |
| DR4w14 | 717.01 combinatorial | YARFQSQTTLKQKT | SEQ. ID NO: 4 | 50 |
| DR5 | Tet Tox 830–843 | QYIKANSKFIGITE | SEQ. ID NO: 5 | 20 |
| DR7 | Tet Tox 830–843 | QYIKANSKFIGITE | SEQ. ID NO: 5 | 25 |
| DR52a | Tet Tox 1272–1284 | NGQIGNDPNRDIL | SEQ. ID NO: 6 | 470 |
| DRw53 | 717.01 combinatorial | YARFQSQTTLKQKT | SEQ. ID NO: 4 | 58 |
| Dr2w2a | Tet Tox 830–843 | QYIKANSKFIGITE | SEQ. ID NO: 5 | 20 |
| DQ3.1 | ROIV | YAHAAHAAHAAHAAHAA | SEQ. ID NO: 7 | 15 |
| IAb | ROIV | YAHAAHAAHAAHAAHAA | SEQ. ID NO: 7 | 28 |
| IAd | Ova 323–326 | ISQAVHAAHAEINE | SEQ. ID NO: 8 | 110 |
| IEd | lambda rep 12–26 | YLEDARRLKAIYEKKK | SEQ. ID NO: 9 | 170 |
| IAs | ROIV | YAHAAHAAHAAHAAHAA | SEQ. ID NO: 7 | 54 |
| IAk | HEL 46–61 | YNTDGSTDYGILQINSR | SEQ. ID NO: 10 | 20 |
| IEk | lambda rep 12–26 | YLEDARRLKAIYEKKK | SEQ. ID NO: 9 | 28 | then it should be understood that the threshold values used to determine good, intermediate, weak, and negative binders should be modified by a corresponding factor.

A "CTL inducing peptide" of the present invention is one derived from selected epitopic regions of potential target antigens, such as tumor associated antigens, including, but not limited to, renal cell carcinoma, breast cancer, carcinoembryonic antigens, melanoma (MAGE-1) antigens, and prostate cancer specific antigen, hepatitis C antigens, Epstein-Barr virus antigens, HIV-1 and HIV-2 antigens, and papilloma virus antigens.

The phrases "isolated" or "biologically pure" refer to material which is substantially or essentially free from components which normally accompany it as found in its native state. Thus, the peptides of the present invention do not contain materials normally associated with their in situ environment, e.g., MHC Class I molecules on antigen presenting cells. Even where a protein has been isolated to a homogeneous or dominant band, there are trace contaminants in the range of 5–10% of native protein which co-purify with the desired protein. Isolated peptides of this invention do not contain such endogenous co-purified protein.

The term "T cell clone" refers to a group of T cells that are progeny of a single virgin lymphocyte and expressing identical immunoglobulin or T cell receptor proteins. The term "virgin" lymphocyte is used here as it is used in Stites et al. Basic and *Clinical Immunology*, 8th Edition, Prentice Hall, Englewood Cliffs, N.J. (1994) which is incorporated herein by reference.

A "T helper peptide" as used herein refers to a peptide recognized by the T cell receptor of T helper cells. The T helper peptides of the present invention are pan DR binding peptides.

DESCRIPTION OF THE PREFERRED EMBODIMENT

In one embodiment, the present invention relates to the use of pan DR peptides to block an immune response by preventing activation of helper T cells. Because of their degenerate class II binding capacity, the Pan DR binding peptides may be used as therapeutics in the inhibition of T cell mediated events involved in allograft rejection, allergic responses, or autoimmunity.

Alternatively, the pan DR peptides are useful as an adjuvant component in any vaccine formulation to enhance an immune response against an administered immunogen. For instance, the pan DR binding peptides are administered with CTL-inducing peptides to induce a CTL response against, e.g., virally infected cells. Alternatively, the pan DR binding peptides are conjugated with a CTL-inducing peptide and administered to induce a CTL response. In another embodiment, the pan DR peptides are conjugated with antibody inducing peptides or admixed with an antibody inducing peptide. The use of helper peptides to enhance antibody responses against particular determinants is described for instance in Hervas-Stubbs et al. *Vaccine* 12:867–871 (1994).

The nomenclature used to describe peptide compounds follows the conventional practice wherein the amino group is presented to the left (the N-terminus) and the carboxyl group to the right (the C-terminus) of each amino acid residue. In the amino acid structure formulae, each residue is generally represented by standard three letter or single letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G.

The peptides of the invention can be prepared in a wide variety of ways. Because of their relatively short size, the peptides can be synthesized in solution or on a solid support in accordance with conventional techniques. Various automatic synthesizers are commercially available and can be used in accordance with known protocols. See, for example, Stewart and Young, *Solid Phase Peptide Synthesis*, 2d. ed., Pierce Chemical Co. (1984), supra.

Alternatively, recombinant DNA technology may be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., *Molecular Cloning, A Laboratory Manual*, Cold Spring Harbor Press, Cold Spring Harbor, N.Y. (1982), which is incorporated herein by reference. Thus, fusion proteins which comprise one or more peptide sequences of the invention can be used to present the appropriate T cell epitope.

As the coding sequence for peptides of the length contemplated herein can be synthesized by chemical techniques, for example, the phosphotriester method of Matteucci et al., *J. Am. Chem. Soc.* 103:3185 (1981), modification can be made simply by substituting the appropriate base(s) for those encoding the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast or mammalian cell hosts may also be used, employing suitable vectors and control sequences.

PAN DR-BINDING PEPTIDES

The present invention provides methods useful for identification of modifications to a starting peptide which broaden its specificity. For instance, International Application WO 92/02543, which is incorporated herein by reference, describes methods suitable for identifying peptides capable of binding DR molecules. This application describes the use of hemagglutinin from the influenza virus ("HA"), as the source of peptides specifically reacting with HLA-DR. Portions of the protein are screened for reactivity to provide sequences which bind the appropriate DR molecule, such as DR1, DR4w4 or DR4w14.

Once an antigen or peptide thereof which binds to the selected MHC molecule is identified, a "core binding region" of the antigen or peptide may be determined by, e.g. synthesizing overlapping peptides, and/or employing N-terminal or C-terminal deletions (truncations) or additions. In the determination of a core binding region and critical contact residues, a series of peptides with single amino acid substitutions may be employed to determine the effect of electrostatic charge, hydrophobicity, etc. on binding.

Within the core region, "critical contact sites," i.e., those residues (or their functional equivalents) which must be present in the peptide so as to retain the ability to bind an MHC molecule and inhibit the presentation to the T cell, may be identified by single amino acid substitutions, deletions, or insertions. In addition, one may also carry out a systematic scan with a specific amino acid (e.g., Ala) to probe the contributions made by the side chains of critical contact residues.

Peptides of the invention which are relatively insensitive to single amino acid substitutions with neutral amino acids, except at essential contact sites, have been found to tolerate multiple substitutions. Particularly preferred multiple substitutions are small, relatively neutral moieties such as Ala, Gly, Pro, or similar residues. The substitutions may be homo-oligomers or hetero-oligomers. The number and types of residues which are substituted or added depend on the spacing necessary between essential contact points and certain functional attributes which are sought (e.g., hydrophobicity versus hydrophilicity). Increased binding affinity for an MHC molecule may also be achieved by such substitutions, compared to the affinity of the parent peptide. In any event, such "spacer" substitutions should employ amino acid residues or other molecular fragments chosen to avoid, for example, steric and charge interference which might disrupt binding.

The effect of single amino acid substitutions may also be probed using D-amino acids. Such substitutions may be made using well known peptide synthesis procedures, as described in e.g., Merrifield, Science 232:341–347 (1986), Barany and Merrifield, The Peptides, Gross and Meienhofer, eds. (N.Y., Academic Press), pp. 1–284 (1979); and Stewart and Young, Solid Phase Peptide Synthesis, (Rockford, Ill., Pierce), 2d Ed. (1984), incorporated by reference herein.

The peptides employed in the subject invention need not be identical to peptides disclosed in the Example section, below, or to a particular antigenic protein sequence of CTL peptides, so long as the subject compounds are able to bind to the appropriate MHC molecules or provide for cytotoxic T lymphocytic activity against the target antigenic protein. Thus, one of skill will recognize that a number of conservative substitutions can be made without substantially affecting the activity of the peptide. Conservative substitutions are those involving replacing an amino acid residue with another which is biologically and/or chemically similar, e.g., one hydrophobic residue for another, or one polar residue for another.

Using the general approach described above, a binding motif for a particular MHC allele can be determined. To broaden the specificity of peptide showing high affinity for one or more alleles, modifications as described above are made and the resulting peptides are further tested for binding. Modified peptides which show significantly higher binding to particular MHC alleles are then selected. The modifications can be made in a more or less random manner. One approach to modifying the starting peptide is to combine binding motifs from two or more alleles.

An other approach may be used in which anchor residues that contain side chains critical for the binding to the MHC are inserted into a poly-alanine peptide of 13 residues. This approach has been used by Jardetzky et al., *Nature* 353, 326–329 (1990), who demonstrated that a polyalanine peptide which was modified with a single dominant MHC contact residue (Tyr) endowed the peptide with high affinity binding capacity for DR1. Instead of using tyrosine as the main MHC contact residue, cyclohexylalanine or phenylalanine can also be utilized. These residues are interchangeable with Tyr with respect to a peptide's capacity to bind those DR alleles capable of high affinity binding of the HA peptide, and furthermore also allow binding to MHC molecules that contained a G→V substitution at residue 86 in the DR β chain. This change affects the binding specificity of the B binding pocket in class II MHC such that tyrosine is no longer capable of binding effectively, whereas cyclohexylalanine, as well as phenylalanine, can bind.

The biological activity of the peptides identified above may be assayed in a variety of systems. Typically, the ability to inhibit antigen-specific T cell activation is tested. In one exemplary protocol, an excess of peptide is incubated with an antigen-presenting cell of known MHC expression, (e.g., DR1) and a T cell clone of known antigen specificity (e.g., tetanus toxin 830–843) and MHC restriction (again, DR1), and the antigenic peptide itself (i.e., tetanus toxin 830–843). The assay culture is incubated for a sufficient time for T cell proliferation, such as four days, and proliferation is then measured using standard procedures, such as pulsing with tritiated thymidine during the last 18 hours of incubation. The percent inhibition, compared to the controls which received no inhibitor, is then calculated.

The capacity of peptides to inhibit antigen presentation in an in vitro assay has been correlated to the capacity of the peptide to inhibit an immune response in vivo. In vivo activity may be determined in animal models, for example, by administering an antigen known to be restricted to the particular MHC molecule recognized by the peptide, and the immunomodulatory peptide. T lymphocytes are subsequently removed from the animal and cultured with a dose range of antigen. Inhibition of stimulation is measured by conventional means, e.g., pulsing with [$^3$H]-thymidine, and comparing to appropriate controls. Certain experimental details will of course be apparent to the skilled artisan. See also, Adorini, et al., *Nature* 334, 623–625 (1988), incorporated herein by reference.

A large number of cells with defined MHC molecules, particularly MHC Class II molecules, are known and readily available from, for instance, the American Type Culture Collection ("Catalogue of Cell Lines and Hybridomas," 6th edition (1988) Rockville, Md., U.S.A., which is incorporated herein by reference.

A preferred embodiment of the peptides of the present invention comprises modifications to the N- and C-terminal residues. As will be well understood by the artisan, the N- and C-termini may be modified to alter physical or chemical properties of the peptide, such as, for example, to affect binding, stability, bioavailability, ease of linking, and the like.

Modifications of peptides with various amino acid mimetics or D-amino acids, for instance at the N- or C-termini, are useful for instance, in increasing the stability of the peptide in vivo. Such peptides may be synthesized as "inverso" or "retro-inverso" forms, that is, by replacing L-amino acids of a sequence with D-amino acids, or by reversing the sequence of the amino acids and replacing the L-amino acids with D-amino acids. As the D-peptides are substantially more resistant to peptidases, and therefore are more stable in serum and tissues compared to their L-peptide counterparts, the stability of D-peptides under physiological conditions may more than compensate for a difference in affinity compared to the corresponding L-peptide. Further, L-amino acid-containing peptides with or without substitutions can be capped with a D-amino acid to inhibit exopeptidase destruction of the antigenic peptide.

Stability can be assayed in a number of ways. For instance, peptidases and various biological media, such as human plasma and serum, have been used to test stability. See, e.g., Verhoef et al., *Eur. J. Drug Metab. Pharmacokin.* 5 11, 291–302 (1986); Walter et al., *Proc. Soc. Exp. Biol. Med.* 148, 98–103 (1975); Witter et al., *Neuroendocrinology* 30, 377–381 (1980); Verhoef et al., *J. Endocrinology* 110, 557–562 (1986); Handa et al., *Eur. J. Pharmacol.* 70, 531–540 (1981); Bizzozero et al., *Eur. J. Biochem.* 122, 251–258 (1982); Chang, *Eur. J. Biochem.* 151, 217–224 (1985), all of which are incorporated herein by reference.

Stability may also be increased by introducing D-amino acid residues at the C and N termini of the peptide. Previous studies have indicated that the halflife of L-amino acid-containing peptides in vivo and in vitro, when incubated in serum-containing medium, can be extended considerably by rendering the peptides resistant to exopeptidase activity by introducing D-amino acids at the C and N termini.

The peptides or analogs of the invention can be modified by altering the order or composition of certain residues, it being readily appreciated that certain amino acid residues essential for biological activity, e.g., those at critical contact sites, may generally not be altered without an adverse effect on biological activity. The non-critical amino acids need not be limited to those naturally occurring in proteins, such as L-α-amino acids, or their D-isomers, but may include non-protein amino acids as well, such as β-γ-δ-amino acids, as well as many derivatives of L-α-amino acids. As discussed, a peptide of the present invention may generally comprise either L-amino acids or D-amino acids, but not D-amino acids within a core binding region.

CTL PEPTIDES

CTL peptides may be administered with the pan DR peptides of the invention to enhance an immune response. CTL epitopes from a number of antigenic proteins can be used in the conjugates of the present invention. Examples of suitable antigens include prostate specific antigen (PSA), hepatitis B core and surface antigens (HBVc, HBVs) hepatitis C antigens, Epstein-Barr virus antigens, melanoma antigens (e.g., MAGE-1), human immunodeficiency virus (HIV) antigens and human papilloma virus (HPV) antigens.

In certain embodiments the CTL peptides of the invention are derived from within the HBV surface antigen or the nucleocapsid polypeptides, core and precore. In more preferred embodiments described herein the CTL-inducing peptides are derived from the region of HBenv$_{309-328}$ (peptide 799.08), HBenv$_{329-348}$ (peptide 799.09) HBenv$_{349-368}$ (peptide 799.10), or the region HBc$_{91-110}$ (peptide 802.03), where the numbering is according to Galibert et al., *Nature* 281, 646 (1979), which is incorporated herein by reference.

CTL peptides comprising the appropriate epitopes are synthesized and then tested for their ability to bind to MHC Class I molecules in assays using, for example, purified class I molecules and radioiodonated peptides and/or cells expressing empty class I molecules by, for instance, immunofluorescent staining and flow microfluorimetry, peptide-dependent class I assembly assays, and inhibition of CTL recognition by peptide competition. Those peptides that bind to the class I molecule are further evaluated for their ability to serve as targets for CTLs derived from infected or immunized individuals, as well as for their capacity to induce primary in vitro or in vivo CTL responses that can give rise to CTL populations capable of reacting with virally infected target cells or tumor cells as potential therapeutic agents.

The one or more CTL peptide may be administered with one or more pan DR peptide/in a mixture which may or may not involve noncovalent associations between the peptides. For instance, one or more of the peptides may be lipidated as described below to facilitate association between the peptides. Alternatively, the peptides may be covalently linked to form a CTL/pan DR conjugate.

To facilitate the association of the CTL peptide with the pan DR peptide, additional amino acids can be added to the termini of the CTL peptide. The additional residues can also be used for coupling to a carrier, support or larger peptide, for reasons discussed herein, or for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide. In addition, the peptide or oligopeptide sequences can differ from the natural sequence by being modified by terminal-NH$_2$ acylation, e.g., by alkanoyl ($C_1$–$C_{20}$) or thioglycolyl acetylation, terminal-carboxy amidation, e.g., ammonia, methylamine, etc. In some instances these modifications may provide sites for linking to a support or other molecule.

As with the pan DR peptides, it will be understood that the peptides of the present invention or analogs thereof which have CTL stimulating activity may be modified to provide other desired attributes, e.g., improved pharmacological characteristics, while increasing or at least retaining substantially all of the biological activity of the unmodified peptide. For instance, the peptides can be modified by extending, decreasing or substituting in the peptides amino acid sequences by, e.g., the addition or deletion of amino acids on either the amino terminal or carboxy terminal end, or both, of peptides derived from the sequences disclosed herein. Usually, the portion of the sequence which is intended to substantially mimic a CTL stimulating epitope will not differ by more than about 20% from the sequence of the target antigenic protein, except where additional amino acids may be added at either terminus for the purpose of modifying the physical or chemical properties of the peptide for, e.g., ease of linking or coupling, and the like. In those situations where regions of the peptide sequences are found to be polymorphic among viral subtypes, it may be desirable to vary one or more particular amino acids to more effectively mimic differing cytotoxic T-lymphocyte epitopes of different viral strains or subtypes.

Within the peptide sequence regions identified by the present invention as containing CTL epitopes, e.g., HBV specific peptides, there are residues (or those which are substantially functionally equivalent) which allow the peptide to retain their biological activity, i.e., the ability to stimulate a class I-restricted cytotoxic T-lymphocytic response against virally infected cells or cells which express viral antigens. These residues can be identified by single amino acid substitutions, deletions, or insertions. In addition, the contributions made by the side chains of the residues can be probed via a systematic scan with a specified amino acid (e.g., Ala). Peptides which tolerate multiple substitutions generally incorporate such substitutions as small, relatively neutral molecules, e.g., Ala, Gly, Pro, or similar residues. The number and types of residues which can be substituted, added or subtracted will depend on the spacing necessary between the essential epitopic points and certain conformational and functional attributes which are sought (e.g., hydrophobicity vs. hydrophilicity). If desired, increased binding affinity of peptide analogues to its MHC molecule for presentation to a CTL can also be achieved by such alterations. Generally, any spacer substitutions, additions or deletions between epitopic and/or conformationally important residues should employ amino acids or other moieties chosen to avoid steric and charge interference which might disrupt binding. Peptides which tolerate substitutions while retaining the desired biological activity may also be synthesized as D-amino acid containing peptides, as described above for Pan DR peptides.

The peptides of the invention can be combined via linkage to form polymers (multimers), or can be formulated in a composition without linkage, as an admixture. Where the same peptide is linked to itself, thereby forming a homopolymer, a plurality of repeating epitopic units are presented. When the peptides differ, e.g., a cocktail representing different viral subtypes, different epitopes within a subtype, different HLA restriction specificities, or peptides which contain T helper epitopes, heteropolymers with repeating units are provided. In addition to covalent linkages, noncovalent linkages capable of forming intermolecular and intrastructural bonds are also contemplated.

PREPARATION OF THE CONJUGATES

As noted above, CTL inducing peptides may be covalently linked to the pan DR-binding peptides to prepare conjugates of the invention. Particularly preferred CTL inducing peptides/pan DR-binding conjugates are linked by a spacer molecule. Alternatively, the CTL peptide may be linked to the pan DR-binding peptide without a spacer. The spacer is typically comprised of relatively small, neutral molecules, such as amino acids or amino acid mimetics, which are substantially uncharged under physiological conditions and may have linear or branched side chains. The spacers are typically selected from, e.g., Ala, Gly, or other neutral spacers of nonpolar amino acids or neutral polar amino acids. In certain preferred embodiments herein the neutral spacer is Ala. It will be understood that the optionally present spacer need not be comprised of the same residues and thus may be a hetero- or homo-oligomer. Preferred exemplary spacers are homo-oligomers of Ala. When present, the spacer will usually be at least one or two residues, more usually three to six residues. In other embodiments the pan DR-binding peptide is conjugated to the CTL peptide, preferably with the pan DR-binding peptide positioned at the amino terminus. The peptides may be joined by a neutral linker, such as Ala-Ala-Ala or the like, and preferably further contains a lipid residue such as palmitic acid or the like (as described further below) which is attached to alpha and epsilon amino groups of a Lys residue ((PAM)$_2$Lys), which is attached to the amino terminus of the peptide conjugate, typically via Ser-Ser linkage or the like.

The CTL inducing peptide may be linked to the pan DR-binding peptide either directly or via a spacer either at the amino or carboxy terminus of the CTL peptide. The amino terminus of either the CTL inducing peptide or the pan DR-binding peptide may acylated. In addition, the CTL peptide/pan DR-binding conjugate may be linked to certain alkanoyl ($C_1$–$C_{20}$) lipids via one or more linking residues such as Gly, Gly-Gly, Ser, Ser-Ser as described below.

In some embodiments it may be desirable to include in the pharmaceutical compositions of the invention at least one component which assists in priming CTL. Lipids have been identified as agents capable of assisting the priming CTL in vivo against viral antigens. For example, palmitic acid residues can be attached to the alpha and epsilon amino groups of a Lys residue and then linked, e.g., via one or more linking residues such as Gly, Gly-Gly-, Ser, Ser-Ser, or the like, to an immunogenic peptide. The lipidated peptide can then be injected directly in a micellar form, incorporated into a liposome or emulsified in an adjuvant, e.g., incomplete Freund's adjuvant. In a preferred embodiment a particularly effective immunogen comprises palmitic acid attached to alpha and epsilon amino groups of Lys, which is attached via linkage, e.g., Ser-Ser, to the amino terminus of the immunogenic peptide.

As another example of lipid priming of CTL responses, E. coli lipoproteins, such as tripalmitoyl-S-glycerylcysteinlyseryl-serine (P$_3$CSS) can be used to prime virus specific CTL when covalently attached to an appropriate peptide. See, Deres et al., Nature 342, 561–564 (1989), incorporated herein by reference. Peptides of the invention can be coupled to P$_3$CSS, for example, and the lipopeptide administered to an individual to specifically prime a CTL response to the target antigen. Further, as the induction of neutralizing antibodies can also be primed with P$_3$CSS conjugated to a peptide which displays an appropriate epitope, the two compositions can be combined to more effectively elicit both humoral and cell-mediated responses to infection.

PHARMACEUTICAL COMPOSITIONS

The pan DR-binding peptides of the present invention and pharmaceutical and vaccine compositions thereof can be administered to mammals, particularly humans, for prophylactic and/or therapeutic purposes. The pan DR peptides can be used to enhance immune responses against other immunogens administered with the peptides. For instance, CTL/pan DR mixtures may be used to treat and/or prevent viral infection and cancer. Alternatively, immunogens which induce antibody responses can be used. Examples of diseases which can be treated using the immunogenic mixtures of pan DR peptides and other immunogens include prostate cancer, hepatitis B, hepatitis C, AIDS, renal carcinoma, cervical carcinoma, lymphoma, CMV and condlyloma acuminatum.

The pan DR-binding peptides may also be used to treat a variety of conditions involving unwanted T cell reactivity. Examples of diseases which can be treated using pan DR-binding peptides include autoimmune diseases (e.g., rheumatoid arthritis, multiple sclerosis, and myasthenia gravis), allograft rejection, allergies (e.g., pollen allergies), lyme disease, hepatitis, LCMV, post-streptococcal endocarditis, or glomerulonephritis, and food hypersensitivities.

In therapeutic applications, the immunogenic compositions or the pan DR-binding peptides of the invention are administered to an individual already suffering from cancer, autoimmune disease, or infected with the virus of interest. Those in the incubation phase or the acute phase of the disease may be treated with the pan DR-binding peptides or immunogenic conjugates separately or in conjunction with other treatments, as appropriate.

In therapeutic applications, compositions comprising immunogenic compositions are administered to a patient in an amount sufficient to elicit an effective CTL response to the virus or tumor antigen and to cure or at least partially arrest symptoms and/or complications. Similarly, compositions comprising pan DR-binding peptides are administered in an amount sufficient to cure or at least partially arrest the symptoms of the disease and its complications. An amount adequate to accomplish this is defined as "therapeutically effective dose." Amounts effective for this use will depend on, e.g., the peptide composition, the manner of administration, the stage and severity of the disease being treated, the weight and general state of health of the patient, and the judgment of the prescribing physician.

Therapeutically effective amounts of the immunogenic compositions of the present invention generally range for the initial immunization (that is for therapeutic or prophylactic administration) from about 1.0 µg to about 5000 µg of peptide for a 70 kg patient, followed by boosting dosages of from about 1.0 µg to about 1000 µg of peptide pursuant to a boosting regimen over weeks to months depending upon the patient's response and condition by measuring specific CTL activity in the patient's blood.

Therapeutically effective amounts of the DR-binding peptides of the present invention generally range from about 0.1 mg to about 2,000 mg of peptide per day for a 70 kg patient, with dosages of from about 0.5 mg to about 1,000 mg of peptide per day being more commonly used.

It must be kept in mind that the compositions of the present invention may generally be employed in serious disease states, that is, life-threatening or potentially life threatening situations. In such cases, in view of the minimization of extraneous substances and the relative nontoxic nature of the conjugates, it is possible and may be felt desirable by the treating physician to administer substantial excesses of these compositions.

For prophylactic use, administration should begin at the first sign of disease or the detection or surgical removal of tumors or shortly after diagnosis in the case of acute infection. This is followed by boosting doses until at least symptoms are substantially abated and for a period thereafter. In chronic infection, loading doses followed by boosting doses may be required.

Treatment of an infected individual with the compositions of the invention may hasten resolution of the infection in acutely infected individuals. For those individuals susceptible (or predisposed) to developing chronic infection the compositions are particularly useful in methods for preventing the evolution from acute to chronic infection. Where the susceptible individuals are identified prior to or during infection, for instance, as described herein, the composition can be targeted to them, minimizing need for administration to a larger population.

The peptide mixtures or conjugates can also be used for the treatment of chronic infection and to stimulate the immune system to eliminate virus-infected cells in carriers. It is important to provide an amount of immuno-potentiating peptide in a formulation and mode of administration sufficient to effectively stimulate a cytotoxic T cell response. Thus, for treatment of chronic infection, a representative dose is in the range of about 1.0 µg to about 5000 µg, preferably about 5 µg to 1000 µg for a 70 kg patient per dose. Immunizing doses followed by boosting doses at established intervals, e.g., from one to four weeks, may be required, possibly for a prolonged period of time to effectively immunize an individual. In the case of chronic infection, administration should continue until at least clinical symptoms or laboratory tests indicate that the viral infection has been eliminated or substantially abated and for a period thereafter.

The pharmaceutical compositions for therapeutic treatment are intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the peptides or conjugates dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of pan DR and/or CTL stimulatory peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The peptides and conjugates of the invention may also be administered via liposomes, which serve to target the conjugates to a particular tissue, such as lymphoid tissue, or targeted selectively to infected cells, as well as increase the half-life of the peptide composition. Liposomes include emulsions, foams, micelies, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes filled with a desired peptide or conjugate of the invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al., Ann. Rev. Biophys. Bioeng. 9, 467 (1980), U.S. Pat. Nos. 4,235,871, 4,501,728, 4,837, 028, and 5,019,369, incorporated herein by reference.

For targeting to the immune cells, a ligand to be incorporated into the liposome can include, e.g., antibodies or fragments thereof specific for cell surface determinants of the desired immune system cells. A liposome suspension containing a peptide or conjugate may be administered intravenously, locally, topically, etc. in a dose which varies according to, inter alia, the manner of administration, the conjugate being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more conjugates of the invention, and more preferably at a concentration of 25%–75%.

For aerosol administration, the peptides are preferably supplied in finely divided form along with a surfactant and propellant. Typical percentages of conjugates are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

In another aspect the present invention is directed to vaccines which contain as an active ingredient an immunogenically effective amount of an immunogenic pan DR peptide or a CTL\pan DR peptide conjugate as described herein. The conjugate(s) may be introduced into a host, including humans, linked to its own carrier or as a homopolymer or heteropolymer of active peptide units. Such a polymer has the advantage of increased immunological reaction and, where different peptides are used to make up the polymer, the additional ability to induce antibodies and/or CTLs that react with different antigenic determinants of the virus or tumor cells. Useful carriers are well known in the art, and include, e.g., thyroglobulin, albumins such as bovine serum albumin, tetanus toxoid, polyamino acids such as poly(lysine:glutamic acid), hepatitis B virus core protein, hepatitis B virus recombinant vaccine and the like. The vaccines can also contain a physiologically tolerable (acceptable) diluent such as water, phosphate buffered saline, or saline, and further typically include an adjuvant. Adjuvants such as incomplete Freund's adjuvant, aluminum phosphate, aluminum hydroxide, or alum are materials well known in the art. And, as mentioned above, CTL responses can be primed by conjugating peptides of the invention to lipids, such as $P_3CSS$. Upon immunization with a peptide composition as described herein, via injection, aerosol, oral, transdermal or other route, the immune system of the host responds to the vaccine by producing large amounts of CTLs specific for the desired antigen, and the host becomes at least partially immune to later infection, or resistant to developing chronic infection.

Vaccine compositions containing the pan DR peptides of the invention are administered to a patient susceptible to or otherwise at risk of disease, such as viral infection or cancer to elicit an immune response against the antigen and thus enhance the patient's own immune response capabilities. Such an amount is defined to be an "immunogenically effective dose." In this use, the precise amounts again depend on the patient's state of health and weight, the mode of administration, the nature of the formulation, etc., but generally range from about 1.0 µg to about 5000 µg per 70 kilogram patient, more commonly from about 10 µg to about 500 µg per 70 kg of body weight.

In some instances it may be desirable to combine the peptide vaccines of the invention with vaccines which induce neutralizing antibody responses to the virus of interest, particularly to viral envelope antigens.

For therapeutic or immunization purposes, the peptides of the invention can also be expressed by attenuated viral hosts, such as vaccinia or fowlpox. This approach involves the use of vaccinia virus as a vector to express nucleotide sequences that encode the peptides of the invention. Upon introduction into an acutely or chronically infected host or into a non-infected host, the recombinant vaccinia virus expresses the immunogenic peptide, and thereby elicits a host CTL response. Vaccinia vectors and methods useful in immunization protocols are described in, e.g., U.S. Pat. No. 4,722, 848, incorporated herein by reference. Another vector is BCG (Bacille Calmette Guerin). BCG vectors are described in Stover et al., Nature 351, 456–460 (1991)) which is incorporated herein by reference. A wide variety of other vectors useful for therapeutic administration or immunization of the peptides of the invention, e.g., Salmonella typhi vectors and the like, will be apparent to those skilled in the art from the description herein.

Antigenic conjugates may be used to elicit CTL ex vivo, as well. The resulting CTL, can be used to treat chronic infections (viral or bacterial) or tumors in patients that do not respond to other conventional forms of therapy, or will not respond to a peptide vaccine approach of therapy. Ex vivo CTL responses to a particular pathogen (infectious agent or tumor antigen) are induced by incubating in tissue culture the patient's CTL precursor cells (CTLp) together with a source of antigen-presenting cells (APC) and the appropriate immunogenic peptide. After an appropriate incubation time (typically 1–4 weeks), in which the CTLp are activated and mature and expand into effector CTL, the cells are infused back into the patient, where they will destroy their specific target cell (an infected cell or a tumor cell).

The peptides of this invention may also be used to make monoclonal antibodies. Such antibodies may be useful as potential diagnostic or therapeutic agents.

The peptides may also find use as diagnostic reagents. For example, a peptide of the invention may be used to determine the susceptibility of a particular individual to a treatment regimen which employs the peptide or related peptides, and thus may be helpful in modifying an existing treatment protocol or in determining a prognosis for an affected individual. In addition, the peptides may also be used to predict which individuals will be at substantial risk for developing chronic infection.

The following examples are offered by way of illustration and not by way of limitation.

EXAMPLES

Example I

Experimental Procedures

I. Cell Lines and MHC Purification

Various cell lines were used as sources of purified human and mouse class II molecules. The following Epstein-Barr virus (EBV) transformed homozygous cell lines were used as sources of human HLA class III molecules (Valli et al., J. Clin. Invest. 91, 616–628, 1993): LG2 [DB1*0101 (DR1)]; 3107 [DRB1*1501 (DR2w2b)]; MAT [DRB1*0301 (DR3)]; PREISS [DRB1*0401 (DR4)]; BIN40 [DRB1*0404 (DRw14)]; SWEIG [DRB1*11011 (DR5)]; PITOUT [DRB1*0701 (DR7)]; PF [DQA1*0301/DQB1*0301 (DQ3.1). In some instances, transfected fibroblasts were used: L416.3 [DRB5*0101 (DR2w2a)]; TR81.19 [DRB3*0101 (DR52a)]; and L257.6 [DRB4*0101 (DRw53)]. For mouse class II molecules, the following cell lines were used: A20 ($IA^d$, $IE^d$) (Sette et al., Science 258, 1801–1804, 1992); CH12 ($IA^k$, $IE^k$) (Sette et al., 1992); LS102.9 ($IA^s$) (Wall et al., Int. Imm. 4, 773–777, 1992); and DB27.4 ($IA^b$) (Wall et al., J. Immuno. 152:4526–4536, 1994).

II. Purification of MHC molecules

MHC molecules were purified essentially as described (Gorga et al., J. Biol. Chem. 262, 16087–16094 (1987)). Briefly, human class II molecules were purified by affinity chromatography using the LB3.1 (all DR, Valli et al., J. Clin. Invest. 91, 616–628 (1993)) or the IVD12 (DQ3.1, Sidney et al., J. Immunol. 152, 4516–4525 (1994)) monoclonal antibodies. Mouse class II molecules were purified by the use of the MKD6 ($IA^d$, Sette et al., Science 258, 1801–1804 (1992)); 10.3.6 ($IA^k$, Sette et al., supra); 14.44 ($IE^d$ and $IE^k$, Sette et al., supra); and Y3JP ($IA^s$, Wall et al., Int. Immunol. 4, 773–777 (1992)) monoclonal antibodies.

III. Peptide Synthesis

Peptides were synthesized by sequential coupling of N-α-Fmoc-protected amino acids on an Applied Biosystems (Foster City, Calif.) 430A peptide synthesizer using standard Fmoc coupling cycles (software version 1.40). All amino acids, reagents, and resins were obtained from Applied Biosystems or Nova Biochem (San Diego, Calif.). Solvents were obtained from Burdick & Jackson. Solid-phase synthesis was started from an appropriately substituted Fmoc-amino acid-Wang resin. The loading of the starting resin was 0.5–0.7 mmol/g polystyrene, and 0.1 or 0.25 meq were used in each synthesis. A typical reaction cycle proceeded as follows: The N-terminal Fmoc group was removed with 25% piperidine in dimethylformamide (DMF) for 5 min, followed by another treatment with 25% in DMF for 15 min. The resin was washed 5 times with DMF. An N-methylpyrolidone (NMP) solution of a 4 to 10-fold excess of a preformed 1-hydroxybenzotriazole ester of the appropriate Fmoc-amino acid was added to the resin, and the mixture was allowed to react for 30–90 min. The resin was washed with DMF in preparation for the next elongation cycle. The fully protected, resin-bound peptide was subjected to a piperidine cycle to remove the terminal Fmoc group. The product was washed with dichloromethane and dried. The resin was then treated with trifluoroacetic acid in the presence of appropriate scavengers [e.g., 5% (v/v) in water] for 60 min at 20° C. After evaporation of excess trifluoroacetic acid, the crude peptide was washed with diethylether, dissolved in water, and lyophilized. The peptides were purified to >95% homogeneity by reverse-phase HPLC using $H_2O/CH_3CN$ gradients containing 0.8% TFA modifier on a Vydac, 300A pore-size, C-18 preparative column. The purity of the synthetic peptides was assayed on an analytical reverse-phase column and their composition ascertained by amino acid analysis and/or sequencing. The cyclohexylalanine used in the synthetic procedures was purchased from Nova Biochem (San Diego, Calif.). Palmitylated peptides were produced by coupling palmitic acid on the resin before cleaving the peptide. Coupling was accomplished by a symmetrical anhydride method, i.e., twofold excess of palmitic acid and one-fold of diisopropylcarbodiimide in dichloromethane for 1 hr.

IV. MHC Peptide Binding Assays

Purified mouse or human class II molecules (5 to 500 nM) were incubated with 5 nM $^{125}$I-radiolabeled peptides for 48 hr in PBS containing 5% DMSO in the presence of a protease inhibitor mixture. Purified peptides were iodinated using the chloramine-T method (Buus, et al., Science 235, 1353–1358 (1987)). The final concentrations of protease inhibitors were: 1 nM PMSF, 1.3 mM 1.10 phenanthrolone, 73 μM pepstatin A, 8 mM EDTA, 6 mM N-ethylmaleimide, and 200 μM Nα-p-tosyl-L-lysine chloromethyl ketone. Final detergent concentration in the incubation mixture was 2.6% digitonin ($IA^d$ and $IA^k$) or 0.05% NP-40 (all other class II molecules). Class II-peptide complexes were separated from free peptide by gel filtration on Sephadex G-50 or TSK2000 columns, and the fraction of peptide bound was calculated as previously described (Sette et al., J. Immunol. 142, 35–40 (1989)). In preliminary experiments, each of the DR preparations was titered in the presence of fixed amounts of radiolabeled peptides to determine the concentration of class II molecules necessary to bind 10 to 20% of the total radioactivity. All subsequent inhibition and direct binding assays were then performed using this class II concentration. In the inhibition assays, inhibitory peptides were typically tested at concentrations ranging from 120 μg/ml to 1.2 ng/ml. The data were then plotted, and the dose yielding 50% inhibition was measured. Each peptide was tested in two to four completely independent experiments.

As used herein binding at <50 nM constitutes high affinity and binding at 50–500 nM constitutes intermediate affinity binding.

V. Inhibition of DR Restricted Peptide Presentation

The capacity of peptides to block the antigen presenting function of MHC was assayed by incubating mitomycin C-treated EBV cells of the appropriate DR type ($5\times10^4$/well) with inhibitor peptides in RPMI 1640 (Bio Whittaker, Walkersville, Md.) in complete medium containing 10% human serum (Gemini Bioproducts, Inc., Calabasas, Calif.). The inhibitor peptides were routinely titrated in 96-well U-bottom plates (Costar, Cambridge, Mass.) over a range of four ten-fold dilutions starting at a concentration of 150 μg/ml. Along with inhibitor peptide, assay wells also received suboptimal concentrations of the HA 307–319 peptide (DR1, DR4w4, DR5, DR52b) or HA 307–319, $Y_{309}$>F (DR4w14), or Lol P1 171–190 (DR3) (Sidney et al., J. Immunol. 149, 2634–2640 (1992)), which, in the absence of inhibitor peptides, resulted in 30–50% of the maximal proliferative response. This concentration was routinely 50 to 200 ng/ml. After incubating APC with peptides for 2 hr at 37° C. in a 5% $CO_2$ incubator, $2 \times 10^4$ T cells were added to each well. The T cell clones used were Cl 1 [DR1 and DR52b (Krieger et al., *J. Immunol.* 146, 2331–2340 (1991))]; Clone 42.19 (DRw14); Clone JK1 (DR5); and line 132-132 (DR3). The proliferation of the T cells was measured three days later. Briefly, 24 hr after T cell addition, [³H]thymidine (1 μCi/well) (ICN, Irvine, Cailf.) was added to each well for a final 18 hr incubation. Cells were then harvested onto glass fiber filters (LKB Wallac cell harvester 1295-001, LKB, Gaithersburg, Md.), and thymidine incorporation (LKB betaplate counter 1205) was measured. The percent inhibition of antigen presentation was calculated for each dose of inhibitor peptide required to inhibit 50% of the proliferative response.

Example 2

DR Binding Specificity of "Universal" Peptide Epitopes

The binding motifs of several murine and human class II MHC alleles have been defined, and motif analysis by sequencing of naturally processed peptides has also recently been described for various class II types (Rudensky et al., *Nature* 353, 622–627 (1991); Chicz et al., *Nature* 358, 764–768 (1992); Hunt et al., *Science* 256, 1817–1820 (1992); Rudensky et al., *Nature* 359, 429–431 (1992)).

In the case of DR molecules in particular, it has been shown (Brown et al., *Nature* 364, 33–39 (1993)) that a large hydrophobic anchor engaging a corresponding hydrophobic pocket of the MHC binding groove is the most crucial determinant of peptide-DR interactions. Several other anchors play definite, albeit less prominent roles and help determine allelic specificity. Recently it has also been emphasized that the peptide backbone of the C-terminal half of the peptide molecule is engaged in direct hydrogen bonding with the walls of the MHC binding groove.

Although the allele-specific polymorphic residues that line the peptide binding pockets of MHC tend to endow each allele with the capacity to bind a unique set of peptides, there are many instances in which a given peptide has been shown to bind to more than one MHC specificity. This has been best documented in the case of the human DR isotype, in which it had been previously noted that several DR alleles appeared to recognize similar motifs, and independently, several investigators reported degenerate binding and/or recognition of certain epitopes in the context of multiple DR types, leading to the concept that certain peptides might represent "universal" epitopes (Busch et al., *Int. Immunol.* 2, 443–451 (1990); Panina-Bordignon et al., *Eur. J. Immunol.* 19, 2237–2242 (1989); Sinigaglia et al., *Nature* 336, 778–780 (1988); O'Sullivan et al., *J. Immunol.* 147, 2663–2669 (1991); Roache et al., *J. Immunol.* 144, 1849–1856 (1991); Hill et al., *J. Immunol.* 147, 189–197 (1991)).

The DR binding capacity of previously described DR binding peptides capable of binding more than one DR molecule (HA 307-319, TT 830-843, CS 378-398, MT 17-31, and HBVnc 50-69 was established using the assay described in Example I, paragraph V. The data obtained (Table II, section A) demonstrate that although these peptides were indeed capable of binding several of the DR molecules tested, they failed to bind to others. For example, the HA 307-319 bound with high (<50 nM) or intermediate (50–500 nM) affinity to DR1, DR4w4, DR5, DR7, and DR2w2a, and weakly to DRw53 (2.2 μM); while no binding was detectable for the remaining four DR specificities. HBVnc 50–69 also bound 5 of the 10 DR specificities tested (DR1, DR2w2b, DR4w4, DR5, and DR2w2a) with high or intermediate affinity. TT 830–843 and CS 378–398 bound with high or intermediate affinity to 4/10 DR molecules tested (DR1, DR5, DR7, DR2w2a and DR1, DR4w4, DR5, DR7, respectively) and MT 17–31 bound with high or intermediate affinity to 3/10 of the DR types.

In conclusion, although these previously described "universal" epitopes bound to several DR types, they were not completely cross-reactive in their binding capacity, in that a maximum of 50% of the DR specificities tested bound a given peptide with high to intermediate affinity.

Example 3

Development of Peptides with High Affinity for Multiple DR Alleles: 760.50 and 760.57

A number of peptides capable of binding with high affinity to the rheumatoid arthritis associated DR alleles DR1, DR4w4, and DR4w14 were generated. To produce these peptides, we used a strategy initially described by Jardetzky et al., *EMBO J.* 9:1797–1803 (1990), in which anchor residues that contain side chains critical for the binding to MHC are inserted into a poly-alanine peptide of 13 residues. Two such peptides, designated 760.50 and 760.57, which are described in copending parent application 08/121,101 and which were particularly interesting with regard to their broad DR binding specificity. When tested for binding to a panel of 10 purified DR molecules, it was found that, in general, these peptides bound with higher affinity and broader specificity than the natural "universal" epitopes described above (Table II, section B). Neither 760.50 nor 760.57 was completely cross-reactive, since only low affinity binding was detected in 4 of the 10 alleles analyzed (DR2w2b, DR3, DR52a, and DRw53). Binding of additional peptides based on 760.50 and 760.57 is shown in Table VI.

TABLE II

Binding Capacity of Various Peptide Epitopes to Different DR Alleles

| Peptide | Sequence | Seq. ID No. | DRβ1 Alleles DR1 | DR2w2b |
|---|---|---|---|---|
| A | | | | |
| HA 307–319 | PKYVKQNTLKLAT | SEQ. ID NO: 1 | 5(1) | —(2) |
| HBVnc 50–69 | PHHTALRQAILCWGELMTLA | SEQ. ID NO: 11 | 70 | 9.1 |
| TT 830–843 | QYIKANSKFIGITE | SEQ. ID NO: 5 | 52 | — |
| CS 378–398 | DIFKKIAKMFKARRVFNVVNR | SEQ. ID NO: 12 | 17 | 1820 |
| MT (Y) 17–31 | YSGPLKAEIAQRLEDV | SEQ. ID NO: 13 | 13 | — |

TABLE II-continued

Binding Capacity of Various Peptide Epitopes to Different DR Alleles

B

| | | | |
|---|---|---|---|
| 760.50 | aA(X)AAAKTAAAAa(3) | 3.1 | 569 |
| 760.57 | aA(X)AAAATLKAAa | 4.5 | 479 |

C

| | | | |
|---|---|---|---|
| 906.09 | aA(X)VAAATLKAAa | 0.61 | 14 |
| 906.11 | aA(X)IAAATLKAAa | 0.38 | 19 |

D

| | | | |
|---|---|---|---|
| 965.10 | aK(X)VAAWTLKAAa | 0.91 | 40 |
| 1024.03 | aKFVAAWTLKAAa | 1.2 | 27 |

| Peptide | DRβ1 Alleles | | | | | DRβ2 Alleles | | |
|---|---|---|---|---|---|---|---|---|
| | DR3 | DR4w4 | DR4w14 | DR5 | DR7 | DR52a | DRw53 | DR2w2a |
| A | | | | | | | | |
| HA 307–319 | — | 45 | — | 118 | 385 | — | 2200 | 45 |
| HBVnc 50–69 | — | 85 | 505 | 263 | 676 | 2765 | ND(4) | 211 |
| TT 830–843 | 3623 | — | — | 20 | 25 | — | — | 20 |
| CS 378–398 | — | 250 | 2272 | 154 | 147 | — | — | 1430 |
| MT (Y) 17–31 | — | — | — | — | 208 | 6266 | 6538 | 350 |
| B | | | | | | | | |
| 760.50 | 6410 | 2.8 | 6.9 | 6.1 | 192 | 9400 | 560 | 57 |
| 760.57 | 2550 | 2 | 3.1 | 5.4 | 78 | — | 3300 | 5 |
| C | | | | | | | | |
| 906.09 | 280 | 2.6 | 5.4 | 2.5 | 76 | 588 | 93 | 2.0 |
| 906.11 | 100 | 2.8 | 3.3 | 2.4 | 31 | 1120 | 41 | 1.3 |
| D | | | | | | | | |
| 965.10 | 86 | 1.1 | 9.1 | 9.1 | 167 | 979 | 75 | 6 |
| 1024.03 | 1470 | 2 | 8 | 18 | 208 | 797 | 420 | 11 |

(1) nM IC50% values
(2) dashes indicate no detectable binding (>10,000 nM)
(3) X = cyclohexyalanine
(4) ND = not done

Example 4

Development of Peptides with High Affinity for Multiple DR Alleles: 906.09 and 906.11

To further broaden specificity the 906.09 and 906.11 peptides were synthesized, in which a V or I was introduced at position 4 of the 760.57 peptide. As shown in Table II, section C, both 906.09 and 906.11 peptides retained the good binding affinity for DR1, DR2w2a, DR4, DR5, and DR7 (in the range of 0.3 to 80 nM). Furthermore, the binding capacity (in comparison to 760.50 and 760.57) for molecules DR2w2b, DR3, DR52a, and DRw53 was significantly improved (10- to 25-fold), with IC50% in the range of 20 to 1200 nM. Thus, 9 of 10 DR specificities bound tested bound these peptides with high or intermediate affinity, and one, DR52a, bound weakly.

In conclusion, these data illustrate the development of peptides binding with high affinity to most, if not all, DR alleles. Because of this broad cross-reactivity pattern amongst different DR molecules, we have determined that the 906.09 and 906.11 peptides are Pan DR binding peptides.

Example 5

Pan DR Binding Peptides Also Bind DQ3.1 and Mouse Class II Molecules

Assays were carried out to determine whether the Pan DR binding peptides were also capable of binding other human class II isotypes or non-human class II molecules. More specifically, the binding capacity of the Pan DR binding peptides to DQ3.1 and several mouse class II specificities was determined, as shown in Table III. For reference purposes, the binding affinities of previously described mouse class II epitopes are also shown in Table III, section A. All of these previously described epitopes bound their relevant restriction elements with high or intermediate affinity, between 20 and 400 nM. It was found that, in general, the 760 series peptides (Table III, section B) bound with intermediate affinity, in the range of 80 to 700 nM, to five of the six alleles tested ($IA^b$, $IA^d$, $IE^d$, $IA^s$, $IE^k$). Interestingly, the 906 series peptides (Table III, section C) bound with significantly higher affinity, in the 10 to 100 nM range in the case of the alleles mentioned above, and 906.11 also bound with intermediate affinity to $IA^k$. With respect to binding to DQ3.1, it was found that 760.50, 760.57, 906.09, and 906.11 all bound with relatively high affinity to purified DQ3.1 molecules (in the 30 to 120 nM range).

As a control, the binding potential of the 760 and 906 peptides to human class I molecules was also examined. No binding was detected, up to 10 μM, to purified HLA-A1, -A2.1, -A3, -A11, and -A24 molecules (data not shown). In conclusion, these data suggest that the 906 series peptides are Pan class II (but not class I) MHC binding peptides.

TABLE III

Capacity of Various Peptide Epitopes to Bind Purified DQ3.1 and Mouse Class II Molecules

| | Peptide/Restriction elements(s) | Sequence | Seq. ID No. | DQ3.1 | IA b | IA d | IE d | IA s | IA k | IE k |
|---|---|---|---|---|---|---|---|---|---|---|
| A | HBVc 126–140/IA b | TPPAYRPPNAPIL | SEQ. ID NO: 14 | ND(1) | 255 | — | — | — | — | — |
| | Ova 323–336/IA d, b | ISQAVHAAHAEINE | SEQ. ID NO: 8 | 577(2) | 400 | 110 | — | 1038 | 1000 | 700 |
| | Lambda rep. 12–26/IE d, k | YLEDARRLKAIYEKKK | SEQ. ID NO: 9 | —(3) | — | 1100 | 170 | — | — | 28 |
| | | HSLGKWLGHPDKF | SEQ. ID NO: 15 | — | >3100 | — | — | 86 | — | — |
| | PLP 139–151/IA s HEL 46–61/IA k | NTDGSTDYGILQINSR | SEQ. ID NO: 16 | 3750 | 7000 | 1222 | 8500 | — | 20 | — |
| B | 760.50 | aA(X)AAAKTAAAAa | | 31 | 200 | 688 | 155 | 491 | 10,00 | 127 |
| | 760.57 | aA(X)AAAATLKAAa | | 94 | 377 | 192 | 172 | 120 | 0 5260 | 78 |
| C | 906.09 | aA(X)VAAATLKAAa | | 48 | 31 | 38 | 31 | 104 | 1333 | 11 |
| | 906.11 | aA(X)IAAATLKAAa | | 115 | 28 | 25 | 13 | 98 | 154 | 14 |
| D | 965.10 | aK(X)VAAWTLKAAa | | 25 | 94 | 733 | 354 | 613 | 3333 | 326 |
| | 1024.03 | aKFVAAWTLKAAa | | 23 | 44 | 1133 | 3056 | 1059 | — | 3500 |

(1) ND = not done
(2) nM IC50% values
(3) dashes indicate no detectable binding (>10,000 nM)

Example 6

Inhibition of T Cell Proliferation by Pan DR Binders

Because of their degenerate class II binding capacity, the Pan DR binders are candidates as therapeutics in the inhibition of T cell mediated events involved in allograft rejection, allergic responses, or autoimmunity. Accordingly, the capacity of these peptides to block an antigen-specific in vitro T cell proliferative response was evaluated. The inhibition of antigen presentation assay described in Example 1, paragraph (V) was used to make these evaluations.

In keeping with their MHC binding capacity, it was found that these peptides were potent inhibitors of the proliferative responses of human T cells restricted by at least six different DR molecules (Table IV). More specifically, peptides 760.50 and 760.57, which have high binding affinities for DR1, DR4w4, DR4w14, and DR5, inhibited T cell proliferation restricted by those alleles, with IC50% in the 1.0 to 25 μm range. By contrast, these peptides bound DR3 molecules only weakly, in the 2.5 to 6.5 μM range, and accordingly, DR3 restricted T cell activation was inhibited poorly (IC50% of 220 μM for 760.57) or not at all (IC50% of >250 μM for 760.50).

The 906.09 and 906.11 peptides also inhibited DR1, DR4w4, DR4w14, and DR5 responses quite effectively (IC50% in the 0.5 to 15 μM range). As expected, the 906 analogs, which have intermediate DR3 binding capacity, were also capable of inhibiting DR3 restricted antigen presentation, with IC50% in the 30 to 60 μM range.

In the same set of experiments, we also tested the 760 and 906 peptides for their capacity to inhibit a DR52b restricted response. This experiment was of interest to us inasmuch as we have not yet been able to develop a molecular binding assay to measure peptide binding to DR52b molecules. The data obtained demonstrate that both 906.09 and 906.11 peptides inhibited the presentation of HA 307–319 Clone 1 in the context of DR52b molecules with good IC50%, in the 1 to 2 μM range, thereby extending to an eleventh allele the Pan DR binding capacity of these peptides.

Finally, these peptides failed to inhibit proliferation of the HA-specific, DR-restricted T cell clone in response to the polyclonal mitogen PHA, and also failed to inhibit in the recently described T cell antagonist assay (De Magistris et al., Cell 68, 525–634 (1992)), in which peptides are added subsequent to (not simultaneously with) the antigenic stimulus (data not shown). These findings rule out the possibility that the results described above might have been caused by some non-specific cytotoxicity of the 760 or 906 peptides.

TABLE IV

Inhibition of T Cell Proliferation by Pan DR Binding Peptides

| | | Activity in inhibition of antigen presentation assay restricted by: | | | | | |
|---|---|---|---|---|---|---|---|
| PEPTIDE | SEQUENCE | DR1 | DR3 | DR4w4 | DR4w14 | DR5 | DR52b |
| 760.50 | aA(X)AAAKTAAAAa | 4.3 (1) | >250 | 3.2 | 2.8 | 25 | >180 |
| 760.57 | aA(X)AAAKTLKAAa | 2.1 | 220 | 0.94 | 0.79 | 18 | 7.5 |
| 906.09 | aA(X)VAAATLKAAa | 0.88 | 31 | 0.58 | 0.43 | 11 | 1.6 |
| 906.11 | aA(X)IAAATLKAAa | 1 | 56 | 0.74 | 0.59 | 13 | 1.7 |

(1) μM IC50%

Example 7

Generation of Pan DR T Cell Epitopes by Modification of Broadly Reactive Class II Binding Peptides A different type of application of Pan DR binding peptides was also considered, namely to use these peptides to produce Pan DR restricted T helper epitopes that could provide help for both humoral and cytotoxic responses. Because all of the potential TCR contact residues in the Pan DR binding peptides were alanines, it was hypothesized that due to the limited interactions the methyl side chains could participate in, introduction of more bulky hydrophobic charged residues might improve the likelihood of interactions with T cell receptors and thereby increase their immunogenicity.

Following this line of reasoning, we further modified the 906.09 Pan DR peptide. Several analogs were generated by introducing bulky or charged side groups at positions 2, 5, and 7, which are potential TCR contact residues based on previous analysis of the HA 307–319 peptide. By contrast, those positions known to influence DR binding were left undisturbed (3, 4, 8, 9, and 11). In addition, analogs were also generated that carried the natural amino acid, Phe, instead of cyclohexylalanine at position 3. These peptides were then tested for retention of their capacity to bind multiple DR alleles, and those peptides that had no significant decrease in their DR binding capacity were then tested for their capacity to induce an immune response. The data from two of the best peptides, 965.10 and 1024.03, are discussed below.

When these two peptides were tested for HLA DR and murine Ia binding (Table II, section D and Table III, section D), it was found that, in general, they retained the high binding capacity and broad reactivity associated with the parent peptide, 906.09, for most DR alleles. The exceptions to this were represented by 1024.03 binding only weakly to DR3 (1470 nM) and also binding with intermediate (420 nM) rather than high affinity to DRw53. Also, the 965.10 and 1024.03 peptides showed greatly reduced binding capacities for most of the murine class II molecules tested. Good binding capacity was retained, however, for the $1A^b$ allele, thus allowing $H-2^b$ mice to be used to test the in vivo immunogenicity of these peptides (see below). Finally, good DQ3.1 binding capacity of both peptides (in the 25 nM range) was also retained.

Example 8

In Vitro Immunogenicity of Pan DR Binding Peptides

The Pan DR epitope 965.10, along with two of its progenitor peptides, 906.09 and 760.50 and the previously described natural epitope, TT 830–843, were compared for their capacity to stimulate in vitro T cell responses in PBMC from normal individuals. The protocol used entailed repeated stimulation of PBL with autologous APC and peptide antigens, and was specifically designed to allow the study of primary in vitro responses. This protocol is provided below, followed by the results of the assays.

A. Assay Protocol

PBMCs from healthy donors were stimulated in vitro using a protocol adapted from Manca et al., *J. Immunol.* 146, 1964–1971 (1991). Peripheral blood mononuclear cells (PBMC) were purified over Ficoll-Paque (Pharmacia LKB, Uppsala, Sweden) and plated in 4 wells of a 24-well tissue culture plate (Costar, Cambridge, Mass.) at $4 \times 10^6$ PBMC/well. The peptides were added at a final concentration of 10 µg/ml. Cultures were then incubated at 37° C., 5% $CO_2$. On day 4, recombinant IL-2 was added at a final concentration of 10 ng/ml. Cultures were routinely fed every three days thereafter by aspirating off 1 ml of media and replacing it with fresh medium containing IL-2. Two additional stimulations of the T cells with antigen were performed on approximately days 14 and 28. The T cells ($3 \times 10^5$/well) were stimulated with peptide (10 µg/ml) using autologous PBMC cells [$2 \times 10^6$ irradiated (7500 rad)/well] as antigen presenting cells in a total of 3 wells of a 24-well tissue culture plate. In addition, on days 14 and 28, T cell proliferative responses were determined as follows: $2 \times 10^4$ T cells/well; $1 \times 10^5$ irradiated PBMC/well as APC; the peptide concentration was titrated between 0.01–10 µg/ml final concentration in U-bottom 96 well tissue culture plates (Costar, Cambridge, Mass.). The T cell proliferation assays were harvested on day 3 as described above.

B. Results

Representative data from three normal donors are shown in FIG. 1. The data obtained following two rounds of stimulation are shown in panels A to C, and after a third round of stimulation, in panels D to F. As predicted, the parental peptides 760.50 and 906.09 were poorly immunogenic in these experiments. Neither peptide induced a significant (>10,000 cpm) response following two rounds of stimulation. After a third round of stimulation, 760.50 induced a response in one donor of the three tested. The natural "universal" epitope TT 830–843 also failed to give a significant response after two rounds of stimulation, and after the third round of stimulation, TT 830–843 also generated a modest positive response in all three donors. In contrast to these weak responses, all three donors responded briskly after only two rounds of stimulation to the modified Pan DR peptide 965.10.

Figure 2A:
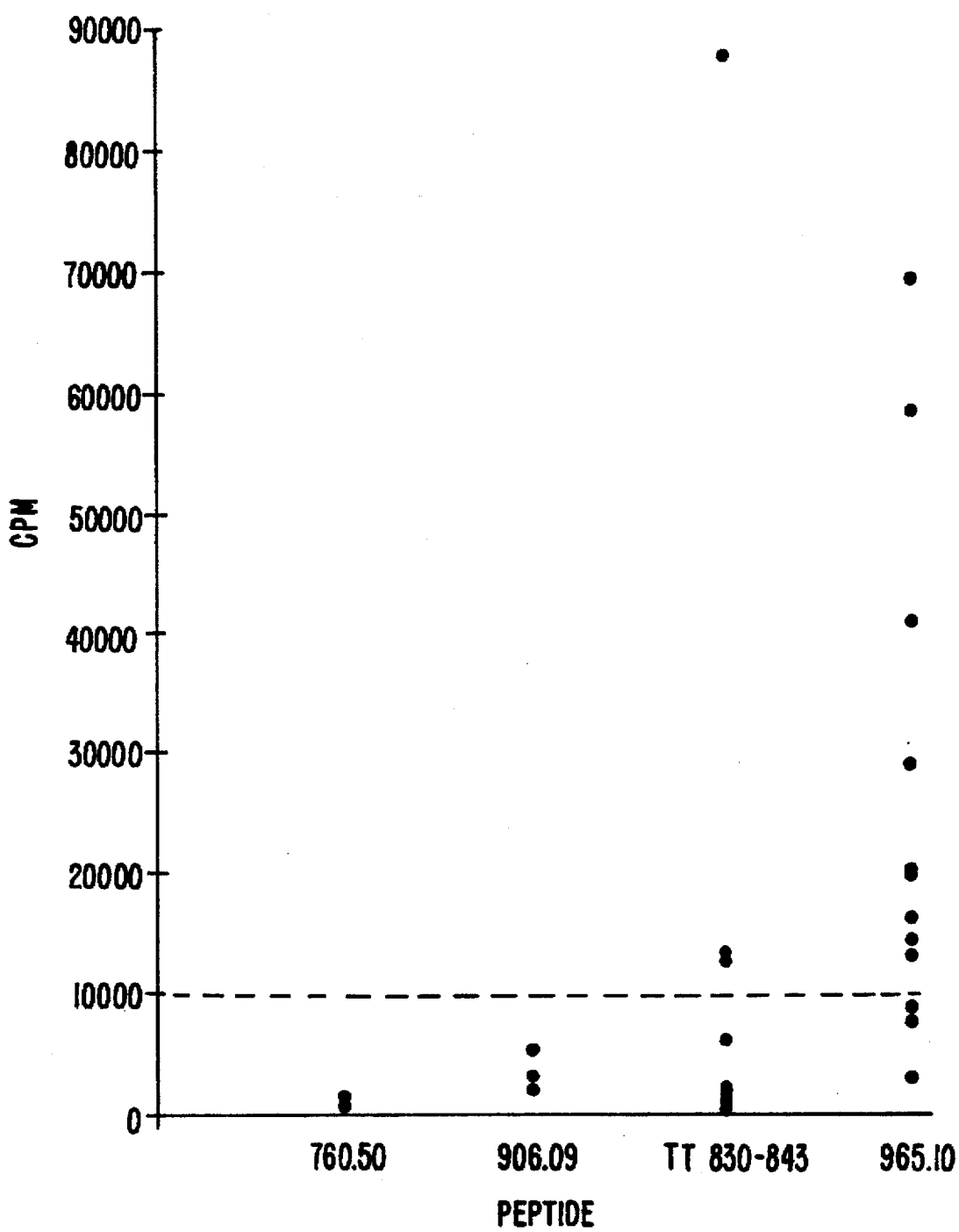
FIGS. 2A and 2B show summaries of antigen specific T cell responses from human PBMC.
Figure 2B:
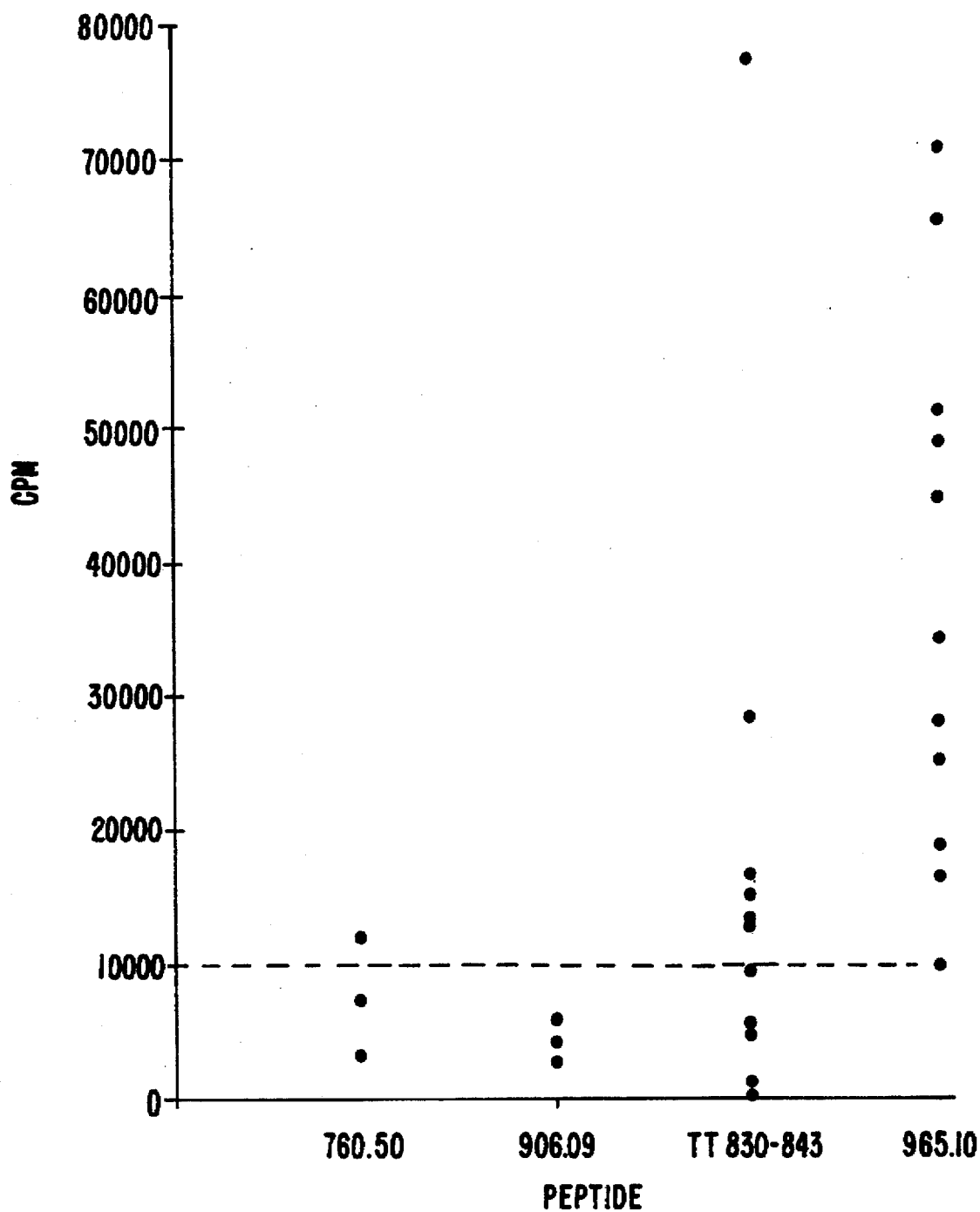
Figure 3A:
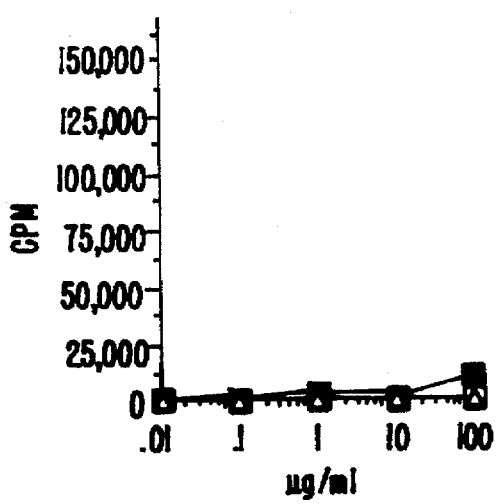
FIGS. 3A–3F show in vivo immunogenicity of various peptide epitopes as measured by proliferative capacity of primed murine lymph node T cells. C57BL/6J mice were injected with 20 μg/mouse (open triangle), 1 μg/mouse (closed square), 50 ng/mouse (open square), 2.5 ng/mouse (closed circle), or 0.125 ng/mouse (open circle) of TT 830–843 (FIG. 3A), Ova 323–336 (FIG. 3B), $HBV_c$ 128–140 (FIG. 3C), 965.10 (FIG. 3D), 1024.03 (FIG. 3E), and 760.50 (FIG. 3F). Ten days later, draining lymph nodes were removed and T cell proliferation assays performed as described in Example 9. A representative of two independent experiments is shown.
Figure 3B:
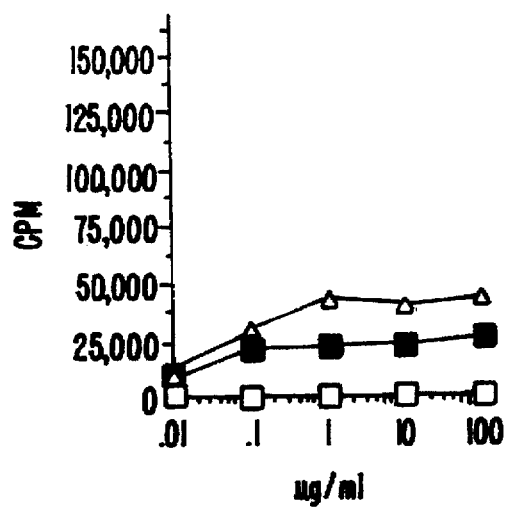
Figure 3C:
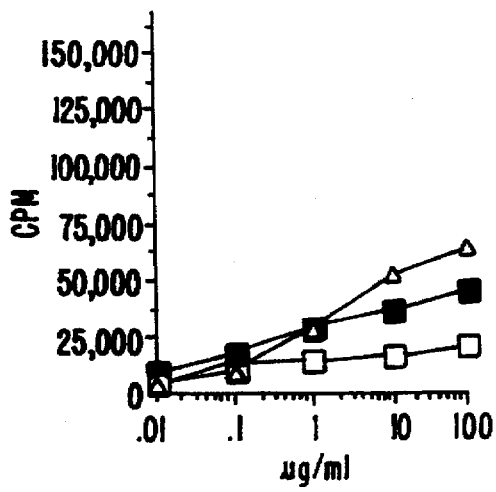
Figure 3D:
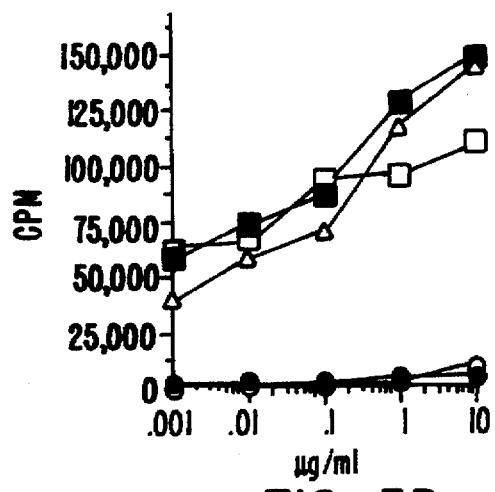
Figure 3E:
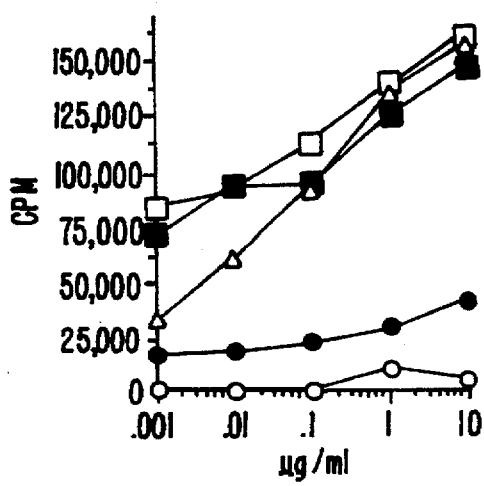
Figure 3F:
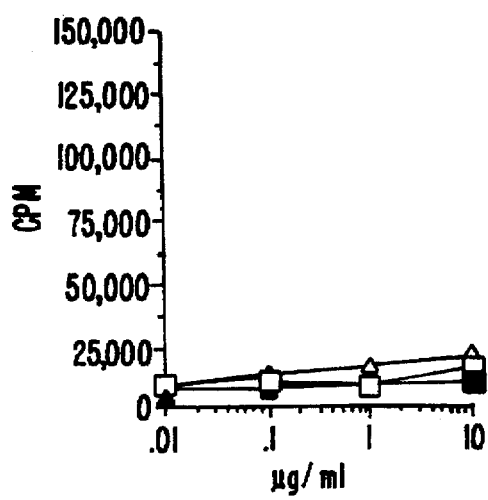

FIGS. 2A and 2B summarize all the in vitro stimulation data that have been obtained (second and third stimulations, respectively). After two in vitro stimulations (FIG. 2A), peptide 965.10 was the only peptide able to significantly stimulate T cells in the majority of donors (9/12). TT 830–843 was able to generate a response in fewer individuals (3/12), while 760.50 and 906.09 both failed to stimulate any response (0/3). By the third stimulation (FIG. 2b) 965.10 generated significant responses in 11 of 12 donors tested, the TT 830–843 was now able to mount a significant response in a majority of the donors (7/12); 760.50 induced a response in 1 of 3 donors, and 906.09 failed to stimulate any of the 3 donors tested.

The ability of 965.10 to expand specific T cell populations in vitro as early as the second stimulation, plus its ability to give a significant T cell response in virtually all of the donors by the third stimulation, demonstrates the superior immunogenic capacity of this peptide relative to peptides TT 830–843, 760.50 or 906.09.

Example 9

Vivo Immunogenicity of the Pan DR Epitopes in Mice

The in vivo immunogenicity of the 760.50, 965.10, and 1024.03 peptides was tested in C57BL/6J ($H-2^b+$) mice.

To carry out these assays, C57BL/6J mice were injected subcutaneously at the base of the tail with a dose titration of various peptides (0.000125, 0.0025, 0.05, 1, and 20 µg/mouse) in PBS/CFA (Difco, Detroit, Mich.) in a 100 µl volume. On day 10, inguinal and paraaortic lymph nodes from groups of three mice/peptide dose were collected, pooled, and homogenized into single cell suspensions. Cells were washed two times and subsequently plated ($1 \times 10^6$ cells/well) in 96-well microtiter tissue culture plates. A log dose peptide titration (0.01 to 100 μg/ml) of the immunizing peptide was added and a standard three day T cell proliferation assay performed as described above.

In these experiments, the activity of the non-natural epitopes to two other previously defined natural $IA^b$ restricted epitopes, Ova 323–336 and HBV core 128–140, were compared. These two natural epitopes bound with a somewhat lower (3 to 14 fold) affinity than 965.10 (Table III, section A). The TT 830–843 peptide, which did not bind $IA^b$ appreciably (data not shown), was included as a negative control. Groups of mice were immunized with varying amounts of peptide (0.000125 to 20 μg/mouse) in CFA. Ten days following immunization, the draining lymph nodes were collected and stimulated in vitro with varying doses of antigen.

As shown in FIG. 3, it was found that, consistent with its inability to bind $IA^b$, TT 830–843 was unable to generate a specific T cell proliferative response. The known $IA^b$ restricted helper epitopes Ova 323–336 (FIG. 3, panel B) and HBVc 125–140 (FIG. 3, panel C) induced responses in the 25,000 to 70,000 cpm range at the two highest peptide doses used for immunization (1 and 20 μg/mouse). The Pan DR epitopes 965.10 (FIG. 3, panel D) and 1024.03 (FIG. 3, panel E) stimulated the strongest responses, with effective immunizing doses being obtained with as little as 0.05 μg/mouse, with a magnitude in the 100,000 to 150,000 cpm range. In contrast, peptide 760.50 (FIG. 3, panel F) was only marginally immunogenic, with a very weak proliferative response being induced, and only at the highest (20 μg/mouse) dose tested. These results indicate that the Pan DR epitopes 965.10 and 1024.03 function as highly effective helper epitopes in vivo, as well as in vitro. Together with the human immunogenicity data, they also suggest that in addition to high MHC binding capacity, the presence of "immunodominant" amino acid residues at potential TCR contact positions is an important element for the generation of vigorous T cell responses.

Example 10

Pan DR Peptides Act as Helper Epitopes For In Vivo CTL Induction in Mice

It is generally assumed that the capacity to induce a T cell proliferative response is an indicator of the helper capacity of a peptide epitope. We sought to verify this by measuring the capacity of the 965.10 peptide to deliver help in the generation of a CTL response. The CTL induction experiments were carried out according to the protocol provided below.

A. CTL induction protocol

Groups of three to six C57 BL/6J mice were immunized by subcutaneous injection at the base of the tail with a mixture of CTL and helper epitopes dissolved in PBS/5% DMSO and emulsified in IFA (Difco, Detroit, Mich.). After 11 days, mice were sacrificed and splenocytes prepared. Splenocytes ($3\times10^7$/10 ml/T25 flask) were simulated in vitro by the addition of peptide-coated syngeneic lipopolysaccaride (LPS) blasts. LPS blasts were prepared 72 hr prior to use from splenocytes of C57BL/6J mice resuspended in medium containing LPS (W E coli 055:B5) (Difco, Detroit, Mich.) (25 μg/ml), and Dextran Sulfate (Pharmacia, Uppsala Sweden) (7 μg/ml). Cultures were prepared with $1.5\times10^6$ splenocytes/ml in a total volume of 3) ml and incubated for 72 hr at 37° C., 5% $CO_2$ in T75 flasks.

Subsequently, cells were irradiated, washed, and resuspended at $30-40\times10^6$ cells/mi. One ml aliquots of this suspension were incubated with the CTL epitope at 100 μg/ml for 1 hr at 37° C., 5% $CO_2$. Cells were washed once and then resuspended at $10\times10^6$ cells/ml. A volume of 1 ml was added per flask to the appropriate effector cells and incubated for 6 days. Cytotoxicity was then measured using EL4 (b haplotype) target cells ($3\times10^6$ cells/ml) which were incubated at 37° C. in the presence of sodium $^{51}Cr$ chromate and CTL epitope peptide. After 60 min, cells were washed three times and resuspended in RPMI-1640 (Bio Whittaker, Walkersville, Md.) containing 10% FCS (Irvine Scientific, Santa Ana, Cailf.), 2 mM L-Glutamine (Irvine Scientific), 50 μg/ml Gentamicin (Irvine Scientific), and $5\times10^{-5}M$ Beta Mercaptoethanol (Sigma, St. Louis, Mo.). Subsequently, $1\times10^{4}$ $^{51}Cr$ labeled target cells were added to a titration of effector cells in U-bottom 96-well plates, final volume=200 μl. After 6 hr incubation at 37° C., 5% $CO_2$, 0.1 ml aliquots of supernatant were removed from each well and radioactivity determined in a Micromedic gamma counter. The percent specific lysis was determined by the following formula: % specific lysis=100×(experimental release−spontaneous release)/(maximum release−spontaneous release). Data are expressed in lytic units/$10^6$ effector cells. One lytic unit is arbitrarily defined as number of lymphocytes required to achieve 30% lysis of $1\times10^4$ $^{51}Cr$-labeled target cells within 6 hr, in absence or presence of peptide.

We immunized C57BL/6J mice with a 10 nm dose of the $K^b$ restricted (Carbonan and Bevan, J. Exp. Med. 169:603–612 (1989)) lipidated CTL determinant (Ova 257–264), along with varying amounts of the $IA^b$ restricted helper epitopes Ova 323–336 (Wall et al., J. Immunol. 152:4526–4536 (1994)), HBV core 128–140, or the 965.10 peptide. After 11 days, spleen cells were stimulated in vitro with the CTL epitope Ova 257–264, incubated for 6 days, and then tested in a standard 6 hr Chromium release CTL assay. The CTL targets included both Ova 257–264 pulsed EL4 cells and Ova 257–264 transfected EG7 cells.

B. Results

The results obtained are shown in Table V. It was found that the Pan DR epitope 965.10 induced a CTL response in a dose-dependent fashion, with an optimum of 307 lytic units observed when 5 μg/mouse of 965.10 peptide was coinjected with the Ova 257–264 CTL epitope. In contrast, the helper activity of the Ova 323–336 and HBVc 128–140 epitopes was much less pronounced, both in terms of the magnitude of the helper effect (four-fold and three-fold increase, respectively) and of the dose required for induction of optimal helper activity (100 μg/mouse).

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

TABLE V

Helper Activity of Various Peptide Epitopes for CTL Induction In Vivo

| T HELPER PEPTIDE | OPTIMAL DOSE OF HELPER PEPTIDE (μg/mouse) | CTL RESPONSE (Δ LYTIC UNITS/E6 CELLS) |
|---|---|---|
| — | — | 12 +/− 2 |
| OVA 323–336 | 100 | 50 +/− 5 |
| HBV core 128–140 | 100 | 35 +/− 10 |
| 965.10 | 5 | 307 +/− 55 |

Specific lysis was calculated as described in Example 10.
A representative of two independent experiments is shown.

TABLE VI

IC50%

| PEPTIDE | SEQUENCE | PCS | DR1 | DR0 | DR4w4 | DR4w14 | DR5 | DR5 | DR2w2 β2 | DR52a | DRw53 | DQ3.1 |
|---|---|---|---|---|---|---|---|---|---|---|---|---|
| 515.01 | PKVVJIBTKJKAT (Seq. ID No. 1) | | 6.1 | — | 42 | — | 153 | 167 | 23 | — | 2190 | — |
| 760.50 | sA(X)AAAKTAAAAa | | 3.8 | 8974 | 2.8 | 7.8 | 7.9 | 159 | 28 | — | 658 | 65 |
| 760.57 | sA(X)AAAATLKAAa | | 1.1 | 3577 | 1.9 | 3.5 | 7.0 | 62 | 2.4 | — | 3327 | 206 |
| 906.01 | sK(X)AAAATLKAAs | 2 | 2.0 | 2054 | 1.8 | 6.6 | 6.3 | 66 | 1.3 | 5917 | ND | 22 |
| 906.02 | sE(X)AAAATLKAAa | | 4.4 | 1877 | 2.8 | 13 | 7.0 | 138 | 2.3 | — | ND | 28 |
| 906.03 | mO(X)AAAATLKAAa | | 2.1 | 1151 | 2.2 | 2.4 | 4.8 | 43 | 0.90 | 8058 | 103 | 14 |
| 906.04 | mV(X)AAAATLKAAa | | 0.56 | 1289 | 2.6 | 4.2 | 3.9 | 98 | 1.1 | — | 31 | 33 |
| 906.05 | mF(X)AAAATLKAAa | | 1.1 | 2128 | 1.8 | 2.8 | 4.4 | 39 | 0.91 | — | ND | 21 |
| 906.13 | aA(X)AKAATLKAAa | 5 | 2.9 | 2211 | 6.8 | 5.1 | 3.8 | 73 | 1.6 | — | 1545 | >2000 |
| 906.14 | mA(X)AEAATLKAAa | | 7.4 | — | 3.9 | 16 | 19 | 266 | 16 | — | ND | 1857 |
| 906.15 | mA(X)aQAATLKAAa | | 3.3 | 5645 | 3.8 | 9.5 | 7.4 | 79 | 0.68 | — | ND | 302 |
| 906.16 | sA(X)AVAATLKAAa | | 1.1 | 854 | 4.0 | 5.4 | 0.1 | 88 | 0.58 | — | 21 | 1857 |
| 906.17 | sA(X)AFAATLKAAa | | 1.8 | 1720 | 4.7 | 5.1 | 4.0 | 27 | 0.54 | — | 52 | 66 |
| 906.18 | sA(X)AAKATLKAAa | 6 | 6.3 | >3500 | 3.2 | 33 | 2.8 | — | 1.8 | — | ND | 302 |
| 906.19 | sA(X)AAEATLKAAs | | 4.1 | 1383 | 4.3 | 4.7 | 8.5 | — | 4.8 | 2191 | 145 | 501 |
| 906.20 | sA(X)AAQATLKAAa | | 1.2 | — | 1.8 | 3.1 | 5.3 | 2105 | 1.7 | — | ND | 565 |
| 906.21 | sA(X)AAVATLKAAa | | 0.28 | — | 2.8 | 4.6 | 4.1 | 34 | 0.77 | — | ND | 371 |
| 906.22 | sA(X)AAFATLKAAa | | 2.1 | — | 2.3 | 3.2 | 4.4 | 66 | 1.7 | — | ND | 1625 |
| 906.23 | sA(X)AAAKTLKAAa | 7 | 0.82 | 2602 | 1.9 | 6.1 | 2.9 | 24 | 0.78 | — | ND | 23 |
| 906.24 | sA(X)AAAEVLKAAa | | 2.5 | 3804 | 2.4 | 6.0 | 14 | 301 | 3.0 | 5108 | ND | 40 |
| 906.25 | sA(X)AAAQTLKAAa | | 1.9 | 2201 | 2.1 | 6.0 | 3.9 | 122 | 0.67 | — | ND | 37 |
| 906.26 | sA(X)AAAVTLKAAa | | 1.2 | 2482 | 2.1 | 4.3 | 5.1 | 53 | 0.74 | ND | ND | 24 |
| 906.27 | aA(X)AAAFTLKAAa | | 0.57 | 4762 | 2.0 | 1.9 | 3.4 | 52 | 1.7 | — | ND | 38 |
| 906.28 | aA(X)AAATTLKAAa | | 2.2 | 3784 | 4.2 | 8.3 | 6.5 | 55 | 0.68 | — | ND | 25 |
| 906.29 | aA(X)AAAATKKaaA | 9 | 3.6 | — | 4.3 | 43 | 10 | 234 | 1.4 | — | ND | 245 |
| 906.30 | aA(X)AAAATEKAAa | | 8.4 | — | 14 | 29 | 67 | 615 | 13 | 4853 | ND | 129 |
| 906.31 | sA(X)AAAATQKAAa | | 0.59 | — | 3.9 | 14 | 15 | 79 | 0.95 | 9861 | ND | 46 |
| 906.32 | sA(X)AAAATVKAAa | | 0.49 | — | 3.1 | 3.5 | 5.5 | 47 | 1.4 | — | ND | 22 |
| 906.33 | sA(X)AAAATFKAAa | | 0.68 | 9091 | 1.4 | 3.3 | 3.1 | 34 | 0.88 | — | ND | 12 |
| 906.34 | sA(X)AAAATIKAAa | | 0.60 | 5303 | 2.1 | 3.3 | 4,1 | 44 | 1.1 | — | ND | 27 |
| 906.35 | mA(X)AAAATLEAAa | 10 | 2.0 | 9062 | 3.5 | 4.4 | 14 | 133 | 7.8 | — | ND | 34 |
| 906.36 | mA(X)AAAATLQAAa | | 2.8 | 3846 | 2.7 | 4.1 | 11 | 96 | 1.8 | — | ND | 21 |
| 906.38 | mA(X)AAAATLFAAa | | 3.3 | — | 2.5 | 7.6 | 25 | 45 | 1.9 | — | ND | 12 |
| 906.39 | sA(X)AAAATLRAAa | | 1.3 | 3004 | 3.2 | 3.3 | 6.5 | 68 | 0.64 | — | ND | 25 |
| 906.47 | aA(X)AAAATLKAEa | 12 | 2.0 | — | 2.5 | 9.2 | 33 | 108 | 2.6 | 4965 | ND | 52 |
| 906.48 | aA(X)AAAATLKAQa | | 0.85 | 9459 | 2.1 | 5.2 | 26 | 77 | 1.1 | 4465 | ND | 16 |
| 906.49 | sA(X)AAAATLKAVa | | 0.72 | 1907 | 3.0 | 3.8 | 8.0 | 23 | 1.1 | 9467 | ND | 13 |
| 906.50 | sA(X)AAAATLKAFa | | 0.42 | 456 | 1.6 | 3.6 | 13 | 60 | 1.8 | 3447 | 75 | 17 |

X = Cyclohexalalanine

---

What is claimed is:

1. A composition comprising a peptide capable of binding antigen binding sites on MHC molecules encoded by substantially all alleles of a DR locus, the peptide consisting of 2 D-amino acids and 11 L-amino acids, said peptide having the formula $R_1—R_2—R_3—R_4—R_5$, proceeding from the amino-terminus to the carboxy-terminus, wherein:

$R_1$ is a D-amino acid followed by alanine or lysine;

$R_2$ is selected from the group consisting of cyclohexylalanine, tyrosine, and phenylalanine;

$R_3$ is 3 or 4 amino acids, wherein each amino acid is independently selected from the group consisting of alanine, isoleucine, serine, glutamic acid and valine;

$R_4$ is selected from the group consisting of threonine-leucine-lysine, lysine-threonine, and tryptophan-threonine-leucine-lysine; and $R_5$ consists of 2 or 4 amino acids followed by a D-amino acid, wherein each of the 2 or 4 amino acids is independently selected from the group consisting of alanine, serine and valine.

2. The composition of claim 1 wherein:

$R_1$ is D-alanine followed by alanine or lysine;

$R_2$ is cyclohexylalanine or phenylalanine;

$R_3$ is 3 or 4 amino acid, wherein each of the 3 or 4 amino acids is selected from the group comprising alanine, isoleucine, and valine; and $R_5$ is 2 or 4 alanines followed by D-alanine.

3. The composition of claim 2 wherein the peptide is selected from the group consisting of aAXAAAKTAAAAa, aAXAAAATLKAAa, aAXVAAATLKAAa, aAXIAAATLKAAa, aKXVAAWTLKAAa, aKFVAAWTLKAAa, aAXAEAATLKAAa, aAXAVAATLKAAa, aAXAAEATLKAAa, aAXAAVATLKAAa, aAXAAAETLKAAa, and aAXAAAVTLKAAa, wherein α is D-alanine, A is alanine, X is cyclohexylalanine, K is lysine, T is threonine, L is leucine, V is valine, E is glutamic acid, I is isoleucine, W is tryptophan, and F is phenylalanine.

4. A pharmaceutical composition comprising a pharmaceutically acceptable carrier and the peptide of claim 1.

5. A composition comprising a CTL inducing peptide and a T helper peptide, wherein the T helper peptide is a peptide of claim 1.

6. The composition of claim 5, wherein the CTL inducing peptide is acetylated, palmitylated, or acylated with a fatty acid.

7. The composition of claim 5, wherein the CTL inducing peptide is linked to the T helper peptide to form a CTL/T helper peptide conjugate.

8. The composition of claim 7, wherein the CTL/T helper peptide conjugate is linked to a carrier.

9. The composition of claim 6, wherein the CTL inducing peptide is linked to the T helper peptide by a spacer molecule.

10. The composition of claim 9, wherein the spacer is Ala-Ala-Ala.

11. A method of inhibiting MHC Class II mediated activation of T cells in a patient, the method comprising administering to the patient a therapeutically effective dose of a pharmaceutical composition comprising a pharmaceutically acceptable carrier and a peptide of claim 1.

12. The method of claim 11 wherein the peptide is the peptide of claim 1.

13. The method of claim 11 wherein the peptide is a peptide of claim 3.

14. A method of inducing MHC Class II mediated activation of T cell clones in a patient, the method comprising administering to the patient a therapeutically effective dose of a pharmaceutical composition comprising a pharmaceutically acceptable carrier and a peptide of claim 1.

15. The method of claim 14 wherein the peptide is conjugated to a CTL inducing peptide.

16. The method of claim 14 wherein the peptide is the peptide of claim 1.

17. The method of claim 14 wherein the peptide is a peptide of claim 3.

18. The method of claim 11 wherein the peptide binds with high affinity to antigen binding sites on MHC Class II molecules encoded by at least about 7 DR alleles selected from the group consisting of DR alleles DR1, 2w2b, 2w2a, 3, 4w4, 4w14, 5, 7, 52a, 52b, 52c, and 53.

19. The method of claim 14 wherein the peptide binds with high affinity antigen to binding sites on MHC Class II molecules encoded by at least about 7 DR alleles selected from the group consisting of DR alleles DR1, 2w2b, 2w2a, 3, 4w4, 4w14, 5, 7, 52a, 52b, 52c, and 53.

20. The method of claim 14, wherein the peptide is linked to a carrier.

21. The method of claim 20, wherein the carrier is tetanus toxoid.

22. The composition of claim 3, wherein the peptide is aAXAAAKTAAAAa.

23. The composition of claim 3, wherein the peptide is aAXAAAATLKAAa.

24. The composition of claim 3, wherein the peptide is a AXVAAATLKAAa.

25. The composition of claim 3, wherein the peptide is aAXIAAATLKAAa.

26. The composition of claim 3, wherein the peptide is aKXVAAWTLKAAa.

27. The composition of claim 3, wherein the peptide is aKFVAAWTLKAAa.

28. The composition of claim 3, wherein the peptide is aAXAEAATLKAAa.

29. The composition of claim 3, wherein the peptide is aAXAVAATLKAAa.

30. The composition of claim 3, wherein the peptide is aAXAAEATLKAAa.

31. The composition of claim 3, wherein the peptide is aAXAAVATLKAAa.

32. The composition of claim 3, wherein the peptide is aAXAAAETLKAAa.

33. The composition of claim 3, wherein the peptide is aAXAAAVTLKAAa.

34. A peptide which binds more than one DR allele, the peptide consisting of the formula $R_1$—$R_2$—$R_3$—$R_4$—$R_5$, proceeding from the amino-terminus to the carboxy-terminus, wherein:

$R_1$ is a D- or an L-amino acid residue followed by alanine or lysine;

$R_2$ is selected from the group consisting of tyrosine, and phenylalanine;

$R_3$ is 3 or 4 amino acids, wherein each amino acid is independently selected from the group consisting of alanine, isoleucine, serine, glutamic acid, and valine;

$R_4$ is selected from the group consisting of threonine-leucine-lysine, lysine threonine, and tryptophan-threonine-leucine-lysine; and $R_5$ consists of 2 or 4 amino acids followed by a D- or an L-amino acid residue, wherein each of the 2 or 4 amino acids is independently selected from the group consisting of alanine, serine and valine.

35. The peptide of claim 34, wherein the peptide is selected from the group consisting of AAXAAAKTAAAAA (SEQ. ID. No. 18), AAXAAAATLKAAA (SEQ. ID. No. 19), AAXVAAATLKAAA (SEQ. ID. No. 20), AAXIAAATLKAAA (SEQ. ID. No. 21), AKXVAAWTLKAAA (SEQ. ID. No. 22), AKFVAAWTLKAAA (SEQ. ID. No. 23), AAXAEAATLKAAA (SEQ. ID. No. 24), AAXAVAATLKAAA (SEQ. ID. No. 25), AAXAAEATLKAAA (SEQ. ID. No. 26), AAXAAVATLKAAA (SEQ. ID. No. 27), AAXAAAETLKAAA (SEQ. ID. No. 28), AAXAAAVTLKAAA (SEQ. ID. No. 29), wherein A is alanine, X is tyrosine or phenylalanine, K is lysine, T is threonine, L is leucine, V is valine, I is isoleucine, W is tryptophan, E is glutamic acid and F is phenylalanine.

36. The peptide of claim 35, wherein the peptide is AAXAAAKTAAAAA (SEQ. ID. No. 18).

37. The peptide of claim 35, wherein the peptide is AAXAAAATLKAAA (SEQ. ID. No. 19).

38. The peptide of claim 35, wherein the peptide is AAXVAAATLKAAA (SEQ. ID. No. 20).

39. The peptide of claim 35, wherein the peptide is AAXIAAATLKAAA (SEQ. ID. No. 21).

40. The peptide of claim 35, wherein the peptide is AKXVAAWTLKAAA (SEQ. ID. No. 22).

41. The peptide of claim 35, wherein the peptide is AKFVAAWTLKAAA (SEQ. ID. No. 23).

42. The peptide of claim 35, wherein the peptide is AAXAEAATLKAAA (SEQ. ID. No. 24).

43. The peptide of claim 35, wherein the peptide is AAXAVAATLKAAA (SEQ. ID. No. 25).

44. The peptide of claim 35, wherein the peptide is AAXAAEATLKAAA (SEQ. ID. No. 26).

45. The peptide of claim 35, wherein the peptide is AAXAAVATLKAAA (SEQ. ID. No. 27).

46. The peptide of claim 35, wherein the peptide is AAXAAAETLKAAA (SEQ. ID. No. 28).

47. The peptide of claim 35, wherein the peptide is AAXAAAVTLKAAA SEQ. ID. No. 29).

48. The peptide of claim 34, wherein the peptide is linked to a carrier.

49. The peptide of claim 48, wherein the carrier is tetanus toxoid.

50. A cell comprising a peptide of claim 34.

51. The cell of claim 50, wherein the peptide is associated with an MHC Class II molecule on the surface of the cell.

52. A cell comprising the peptide of claim 48.

53. A method of inducing MHC Class II mediated activation of T helper cells, the method comprising contacting a peptide of claim 34 with the T helper cells.

54. The method of claim 53, wherein the peptide is contacted with T helper cells in vitro.

55. The method of claim 53, wherein the T helper cells mediate a CTL response.

56. The method of claim 53, wherein the T helper cells mediate an antibody response.

* * * * *

Disclaimer 5,736,142 - Alessandro Sette, La Jolla; Federico Gaeta, Foster City; Howard M. Grey; John Sidney, both of La Jolla; Jeffrey L. Alexander, Encinita, all of California. ALTERATION OF IMMUNE RESPONSE USING PAN DR-BINDING PEPTIDES. Patent dated April 7, 1998. Disclaimer filed May 17, 1999, by the assignee Epimmune, Inc.

Hereby enters this disclaimer to claims 1, 2, 3, 4, 11, 12, 13, 22, 23, and 34 of said patent.
*(Official Gazette,* July 27, 1999)